United States Patent
Suzuki et al.

(10) Patent No.: US 10,342,527 B2
(45) Date of Patent: Jul. 9, 2019

(54) REPEATING-TYPE ORGAN-FASTENING TOOL

(71) Applicants: SUMITOMO BAKELITE CO., LTD., Tokyo (JP); Yutaka Suzuki, Tokyo (JP)

(72) Inventors: Yutaka Suzuki, Tokyo (JP); Kazuki Okada, Akita (JP); Shinetsu Harata, Akita (JP); Kiyotaka Arikawa, Akita (JP); Yasunori Kojo, Akita (JP)

(73) Assignee: SUMITOMO BAKELITE COMPANY LIMITED, Tokyo (JP)

( * ) Notice: Subject to any disclaimer, the term of this patent is extended or adjusted under 35 U.S.C. 154(b) by 787 days.

(21) Appl. No.: 14/764,429

(22) PCT Filed: Feb. 20, 2014

(86) PCT No.: PCT/JP2014/054062
§ 371 (c)(1),
(2) Date: Jul. 29, 2015

(87) PCT Pub. No.: WO2014/129554
PCT Pub. Date: Aug. 28, 2014

(65) Prior Publication Data
US 2015/0374358 A1    Dec. 31, 2015

(30) Foreign Application Priority Data

Feb. 22, 2013 (JP) .................. 2013-033027
Mar. 22, 2013 (JP) .................. 2013-059321

(51) Int. Cl.
*A61B 17/04* (2006.01)
*A61B 17/00* (2006.01)
(Continued)

(52) U.S. Cl.
CPC ...... *A61B 17/0469* (2013.01); *A61B 17/0401* (2013.01); *A61B 17/0218* (2013.01);
(Continued)

(58) Field of Classification Search
CPC ............ A61B 17/0401; A61B 17/0469; A61B 2017/06052; A61B 2017/0409;
(Continued)

(56) References Cited

U.S. PATENT DOCUMENTS 6,056,771 A * 5/2000 Proto ................. A61B 17/0469
606/222
2004/0249393 A1* 12/2004 Weisel ............. A61B 17/06109
606/144
(Continued)

FOREIGN PATENT DOCUMENTS

EP    0 647 431 A2    4/1995
EP    2 149 337 A2    2/2010
(Continued)

OTHER PUBLICATIONS

International Search Report dated May 20, 2014, issued in counterpart application No. PCT/JP2014/054062 (4 pages).

*Primary Examiner* — Diane D Yabut
*Assistant Examiner* — Majid Jamialahmadi
(74) *Attorney, Agent, or Firm* — Westerman, Hattori, Daniels & Adrian, LLP

(57) ABSTRACT

There is provided a repeated type organ fixing instrument having a plurality of suturing tools. The organ fixing instrument includes a rod-shaped engaging portion, a suture fixed to the engaging portion, a puncture needle for housing a plurality of the engaging portions. A plurality of the engaging portions are extruded one by one from the puncture needle by the operation of a operation unit main body. The suture fixed to at least one of the plurality of engaging portions is inserted within the inside of the puncture needle and wherein the other suture is derived from the inside to the outside of the puncture needle.

14 Claims, 33 Drawing Sheets

(51) Int. Cl.
*A61B 17/06* (2006.01)
*A61B 17/02* (2006.01)

(52) U.S. Cl.
CPC . *A61B 17/0482* (2013.01); *A61B 2017/00818* (2013.01); *A61B 2017/047* (2013.01); *A61B 2017/0409* (2013.01); *A61B 2017/0417* (2013.01); *A61B 2017/0454* (2013.01); *A61B 2017/0464* (2013.01); *A61B 2017/06052* (2013.01)

(58) Field of Classification Search
CPC .... A61B 2017/0445; A61B 2017/0417; A61B 2017/0419; A61B 2017/0454; A61B 2017/0448
See application file for complete search history.

(56) References Cited

U.S. PATENT DOCUMENTS

| | | | |
|---|---|---|---|
| 2007/0073321 A1 | 3/2007 | Mikkaichi et al. | |
| 2009/0082786 A1 | 3/2009 | Surti | |
| 2009/0088797 A1* | 4/2009 | Crombie | A61B 17/0401 606/232 |
| 2009/0157099 A1 | 6/2009 | Surti | |
| 2009/0222039 A1* | 9/2009 | Dreyfuss | A61L 27/08 606/229 |
| 2010/0004665 A1* | 1/2010 | Hong | A61B 17/0401 606/148 |
| 2010/0204731 A1 | 8/2010 | Hart et al. | |
| 2010/0256679 A1* | 10/2010 | Ducharme | A61B 17/0057 606/232 |
| 2012/0290006 A1* | 11/2012 | Collins | A61B 17/0401 606/232 |

FOREIGN PATENT DOCUMENTS

| | | |
|---|---|---|
| JP | 8-173436 A | 7/1996 |
| JP | 2006-116356 A | 5/2006 |
| JP | 2006-296914 A | 11/2006 |
| JP | 2006-304928 A | 11/2006 |
| JP | 2010-512820 A | 4/2010 |
| JP | 2010-154883 A | 7/2010 |
| JP | 2010-179102 A | 8/2010 |
| JP | 2010-273933 A | 12/2010 |
| JP | 2011-182986 A | 9/2011 |
| KR | 10-2006-0009698 A | 2/2006 |
| WO | 2007/037326 A1 | 4/2007 |
| WO | 2008/075211 A1 | 6/2008 |
| WO | 2009/158246 A1 | 12/2009 |

* cited by examiner

REPEATING-TYPE ORGAN-FASTENING TOOL

TECHNICAL FIELD

The present invention mainly relates to an organ fastening tool used for gastrostomy (PEG: percutaneous endoscopic gastrostomy).

The present application claims priority on the basis of Japanese Patent Application No. 2013-033027, filed in Japan on Feb. 22, 2013, and Japanese Patent Application No. 2013-059321, filed in Japan on Mar. 22, 2013, the contents of which are incorporated herein by reference.

BACKGROUND ART

In previous gastrostomy, two puncture needles were punctured from the body surface to the stomach wall, a suture was inserted from one of the puncture needles, and the suture was hooked by the loop body which was inserted from the other needle and captured, thereby forming the loop. Stomach is lifted by pulling the looped suture, and the body wall and the stomach wall are fixed by further tying the sutures together with each other. Thereafter, the large through hole is formed in the body wall and the stomach wall by deeply puncturing the guidewire and dilator from the body surface, and the stomach fistula is established by indwelling the indwelling catheter there.

In a general gastrostomy, it is necessary to fix the body wall and the stomach wall is in at least three positions (possibly four positions) so as to surround the gastrostomy scheduled portion. After the stomach fistula is established, the sutures are cut and removed.

This method is a highly invasive because it is necessary to puncture the two puncture needles in respective fixing positions, and in some cases it is difficult to capture the suture by the loop body in the stomach due to the skill of the doctor.

On the other hand, it became possible to be low invasive and easy procedure according to the instrument of Patent Document 1 (prior art), since the stomach wall can be fixed to the body wall by only one puncture needle, as shown in FIG. 11, and the like. According to this procedure, it became unnecessary to loop the suture since the procedure can be performed with a single puncture needle by inserting T-shaped suture instrument in which the suture is engaged with the center of the rod-shaped engaging portion rod and lifting the stomach wall, instead of tying the two sutures.

The instrument of Patent Document 1 takes a form in which it is possible to individually push out a plurality of suture instruments housed in the internal portion of the puncture needle (hereinafter referred to as repeating type). Specifically, four suture instruments are housed in the puncture needle. Thus, upon fixing the gastric wall to the body wall at three to four positions in one procedure, it is possible to achieve this with one instrument. Therefore, it is easy because the replacement operation such as discarding, opening or switching of the instrument becomes unnecessary.

In the suturing tool of Patent Document 1, one suture is engaged with the engaging portion. When fixing the suturing tool to the body surface, the suture is tied together with the suture of the other suture instrument on the body surface.

Similarly, in Patent Document 2, an organ fixing instrument using a T-shaped suture instrument is described. This instrument uses a suture instrument in which one looped suture is engaged with the rod-shaped engaging portion (rod). This organ fixing instrument takes a form in which only one suturing tool is equipped with in the internal site of the puncture needle (hereinafter referred to as single-type). The pad-like cushioning material is attached to the suture. The cushioning material is pressed against to the body surface, and the sutures entangled with each other are tied to the cushion material in a state of the two strings by cutting the suture loop. Thus, it is possible to fix each individual suture instrument to the body surface at 3 to 4 points of the fixed locations.

PRIOR ART DOCUMENTS

Patent Documents

Patent Document 1: Japanese Patent Application Publication No. 2006-296914

Patent Document 2: Japanese Patent Application Publication No. 2010-154883

DISCLOSURE OF THE INVENTION

Problems to be Solved by the Invention

The organ fixing instrument of Patent Document 1 has a problem in which the sutures easily entangled each other because all of four sutures are inserted into the interior of the puncture needle. When the sutures tangle, there is a possibility in which the other locking part is also withdrawn when attempted to withdraw the puncture needle from the body wall by extruding the engaging portion of the tip from the puncture needle.

Furthermore, the organ fixing instrument of Patent Document 1 has a problem in which the puncture needle is thick and highly invasive. That is to say, in the organ fixing instrument of Patent Document 1, four sutures are dispersedly arranged around the top, that is the locking portion which goes through the inside of the puncture needle of the extrusion apparatus side when accommodating the four suture instruments in the interior of the puncture needle. Therefore, the inner diameter of the puncture needle is required in the dimension of at least, in addition to the outer diameter of the engaging portion, the sum of the thickness of the two sutures on the both sides. Thus, the outer diameter of the puncture needle of the organ fixing instrument of Patent Document 1 is thick compared with that of the single type which contains only one suturing device.

Accordingly, in the instrument of Patent Document 1, there is a risk of difficult operation due to tangled sutures, and there is a problem of highly invasive due to thick puncture needle, although there is a benefit of the procedure caused by the repeating type.

Furthermore, in the organ fixing instrument of Patent Document 2, one instrument is required for each fixing point between the stomach wall and the body wall since it is a single type. The replacement of the instrument is complicated, and there is a problem of high cost.

The present invention has been made in view of the above problems. The present invention has the benefits of repeated type in which the replacement works such as discarding, opening or switching of the instrument are reduced and simple. In addition, the present invention provides the organ fixing instrument capable of improving the stability of operation by suppressing the entanglement of the sutures than the conventional repeating type organ fixing instrument and realizing low invasion caused by thinning the puncture needle.

Means for Solving the Problems

According to the first aspect of the present invention, a repeating type organ fixing instrument which has a plurality of suture instruments comprising a rod-shaped engaging portion and a suture which is connected to the engaging portion, and a puncture needle accommodating a plurality of the engaging portions, in which the plurality of engaging portions are extruded from the puncture needle one by one by the operation of the operating main unit, is provided, wherein the suture connected to at least one of the plurality of engaging portions is inserted into the inside of the puncture needle, and the other suture is provided to the outside from the inside of the puncture needle.

According to the second aspect of the present invention, a repeating type organ fixing instrument which has a suture instrument comprising a rod-shaped engaging portion and a plurality of sutures which are connected to the engaging portion at their ends, and a puncture needle accommodating a plurality of the engaging portions side by side in the tip base end direction, in which the plurality of engaging portions are extruded from the puncture needle one by one by the operation of the operating main unit, is provided, wherein the yarn passage for inserting the suture housed in the tip end side of the suturing tool in the puncture needle is formed at the engaging portion of the other suturing tool housed in the base end.

Effects of the Invention

According to the first aspect of the present invention, it is possible to reduce the number of the sutures going through the interior of the puncture needle. Therefore, a repeating type organ fixing instrument in which the stability of the operation due to a decrease in entanglement of the sutures in the interior of the puncture needle is improved, is provided, wherein it is possible to prevent expansion of the outer diameter of the puncture needle.

According to the second aspect of the present invention, it is possible to insert a suture into the interior of the puncture needle through the yarn passage formed at the engaging portion. Thus, while having the advantages of the repeated type, low invasive organ fixing instrument can be realized because it is possible to reduce the diameter of the puncture needle.

BEST MODE FOR CARRYING OUT THE INVENTION

First Aspect

Figure 1:
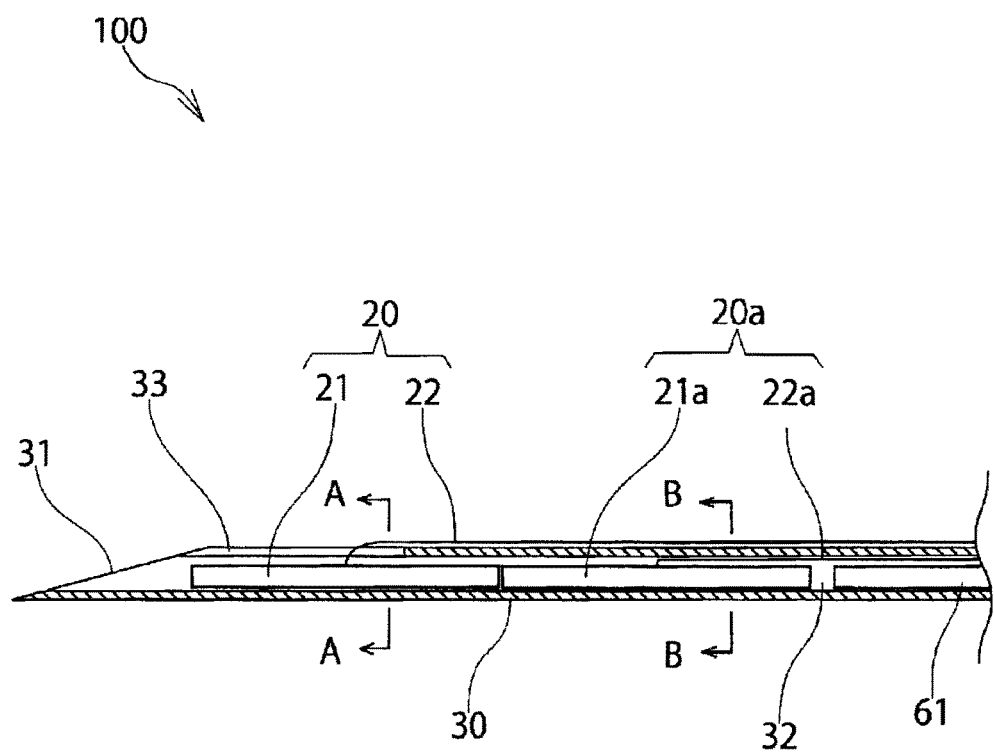
FIG. 1 A partial sectional view showing the organ fixing instrument of the first embodiment of the first aspect of the present invention.

The following is a description of the embodiments of the first aspect of the present invention on the basis of the drawings. In the drawings, the same reference numerals are given to the same components, the duplicate description may be omitted in some cases.

First Embodiment

Figure 2:
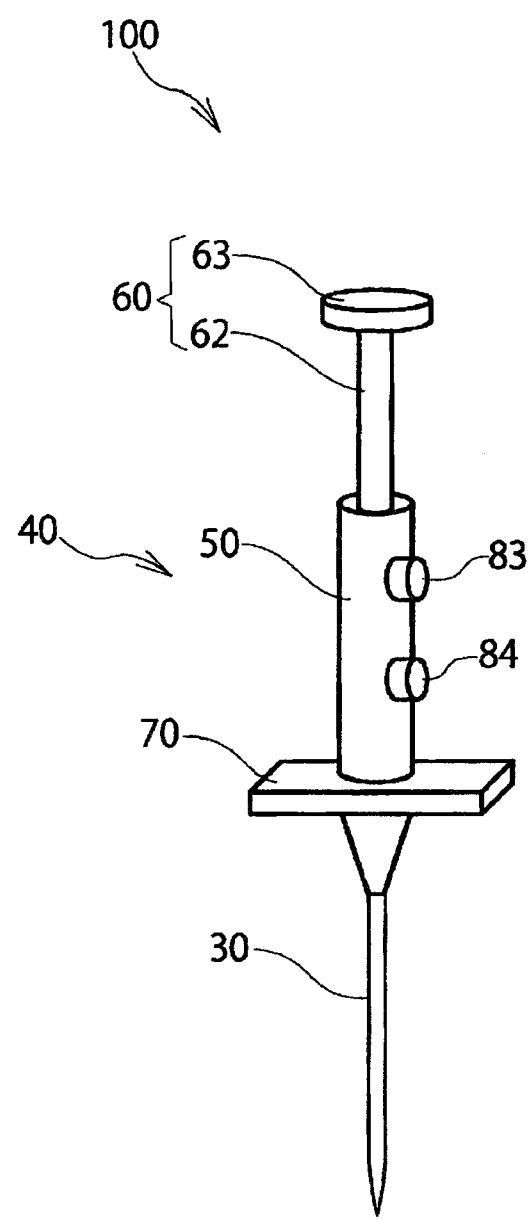
FIG. 2 A schematic perspective view showing the organ fixing instrument of the first embodiment of the first aspect.
Figure 3:
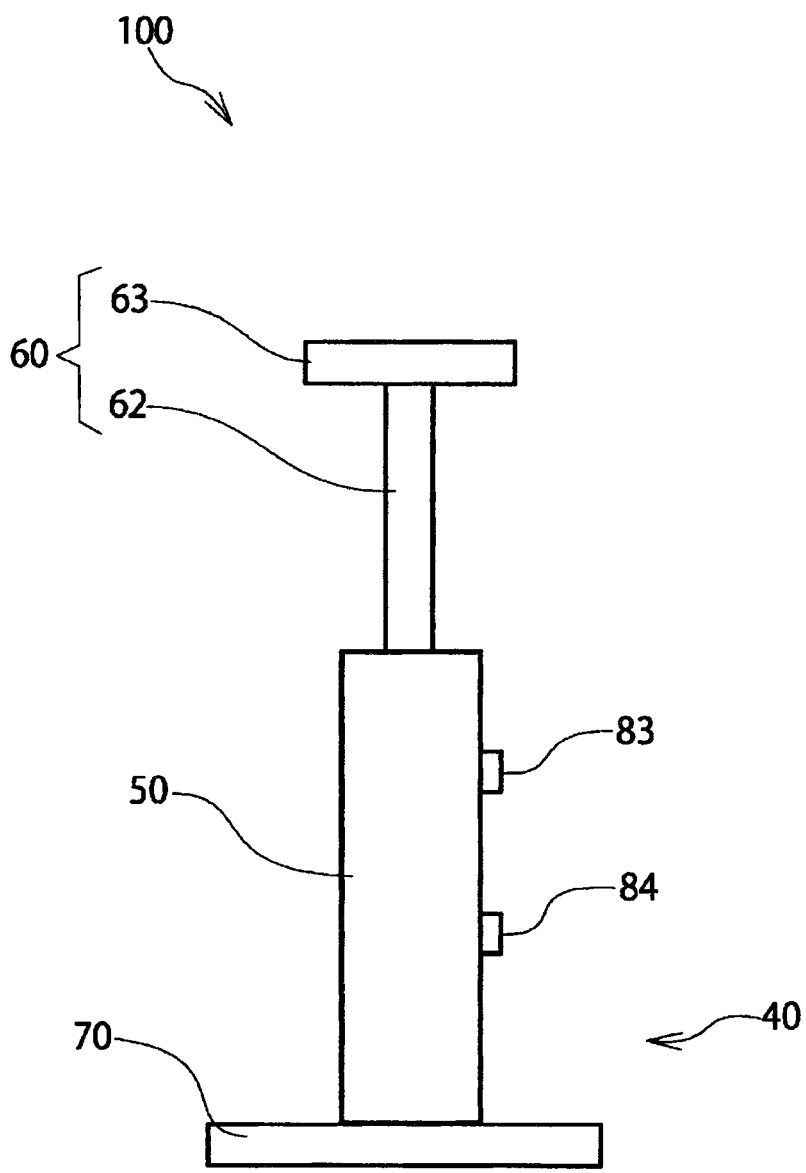
FIG. 3 A partial side view of the organ fixing instrument of the first embodiment of the first aspect.
Figure 4:
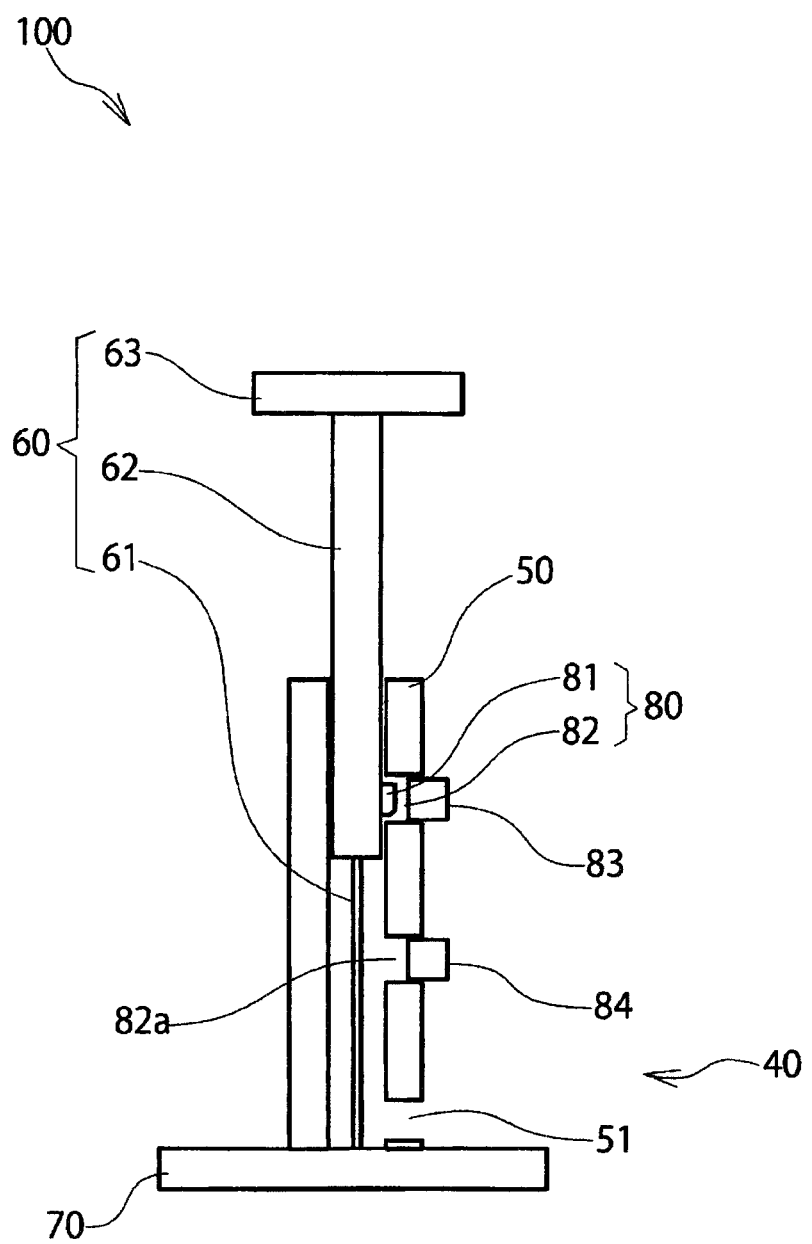
FIG. 4 A partial perspective view showing the internal mechanism of the organ fixing instrument of the first embodiment of the first aspect.
Figure 5:
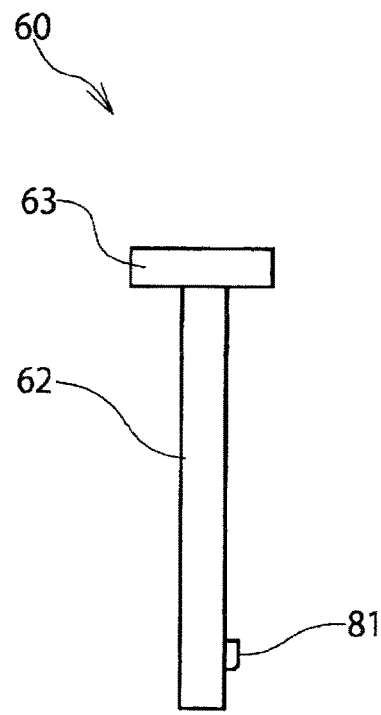
FIG. 5 A side view showing the operating portion of the first embodiment of the first aspect.
Figure 6:
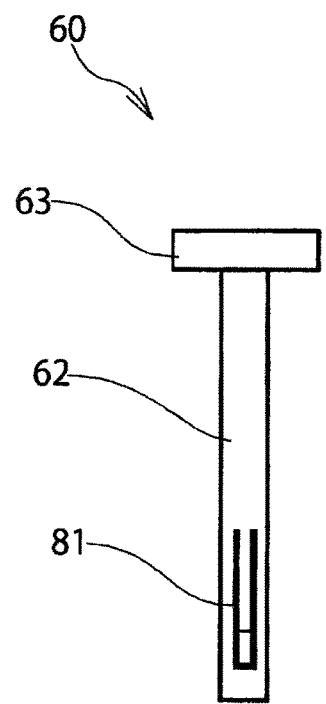
FIG. 6 Another side view showing the operating portion of the first embodiment of the first aspect.
Figure 7:
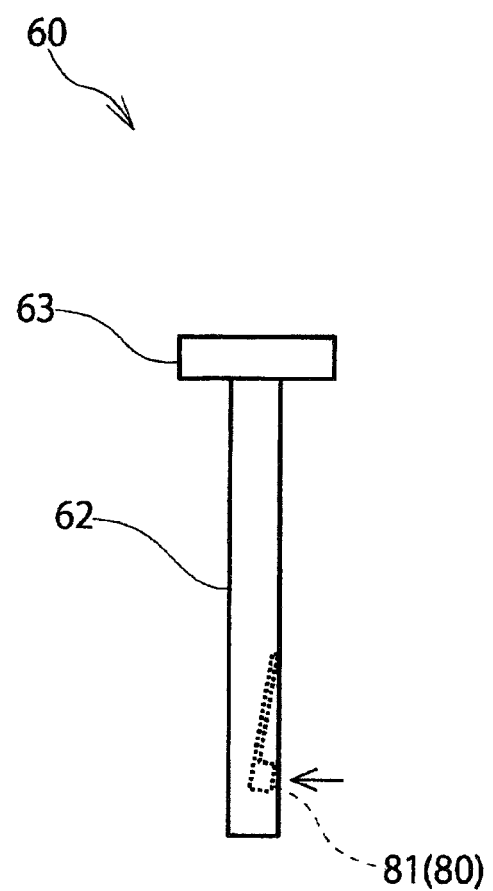
FIG. 7 A side view showing a state in which the engaging claw of the operating portion of the first embodiment of the first aspect is pushed.
Figure 8:
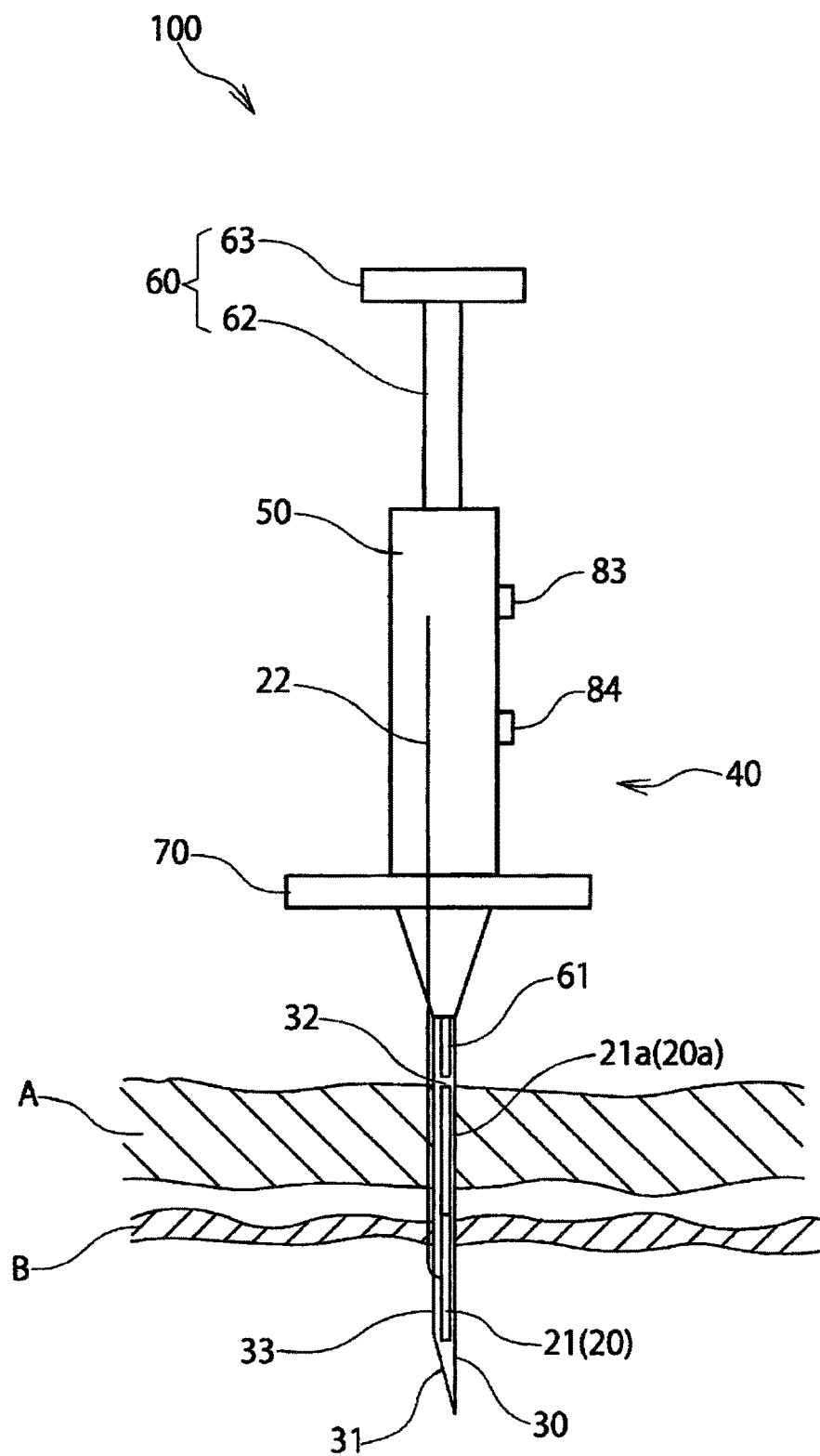
FIG. 8 A sectional view showing a state in which the organ fixing instrument of the first embodiment of the first aspect is punctured in the abdomen.
Figure 9:
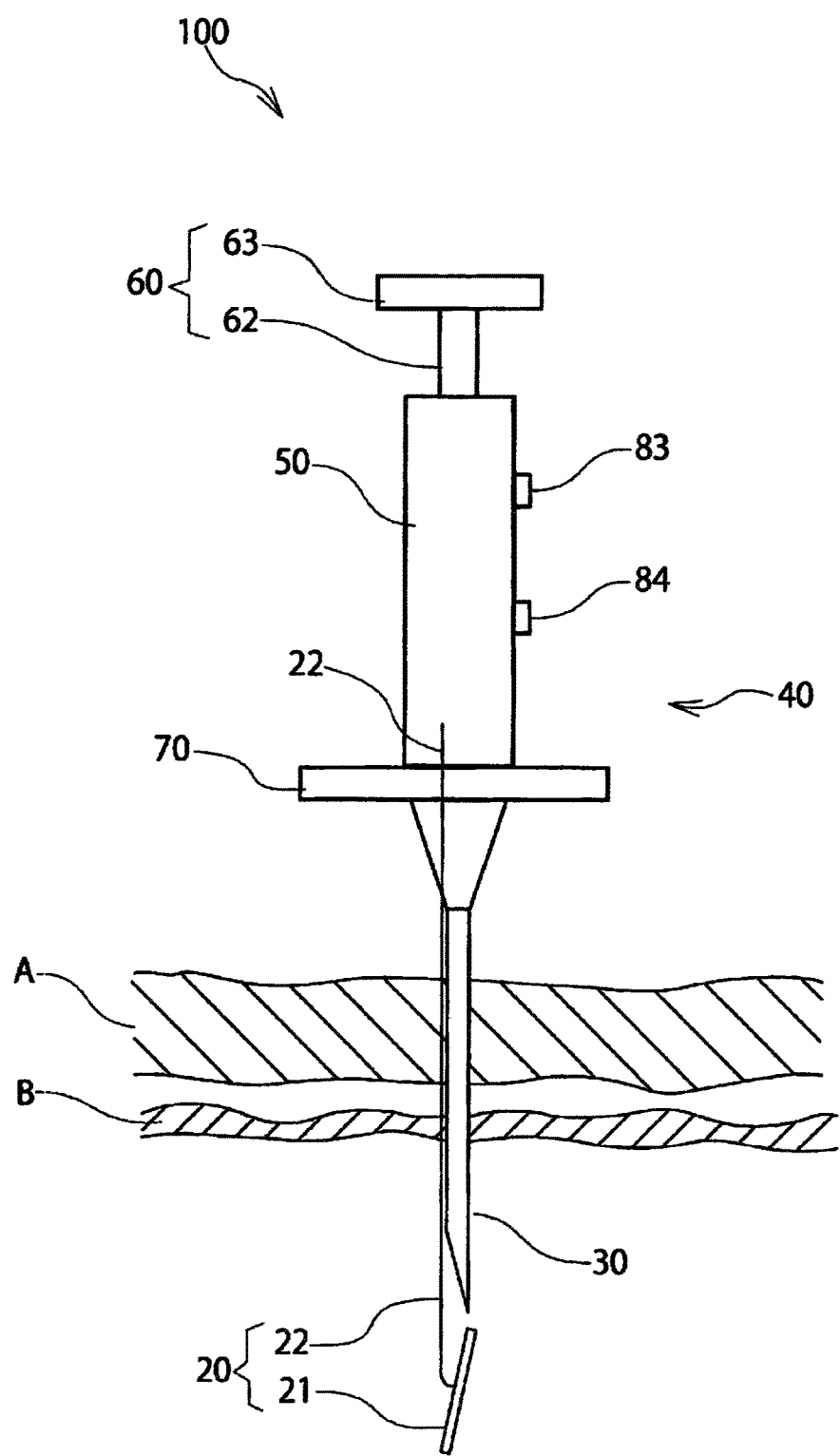
FIG. 9 A sectional view showing a state in which the operating portion of the organ fixing instrument of the first embodiment of the first aspect comes down.
Figure 10:
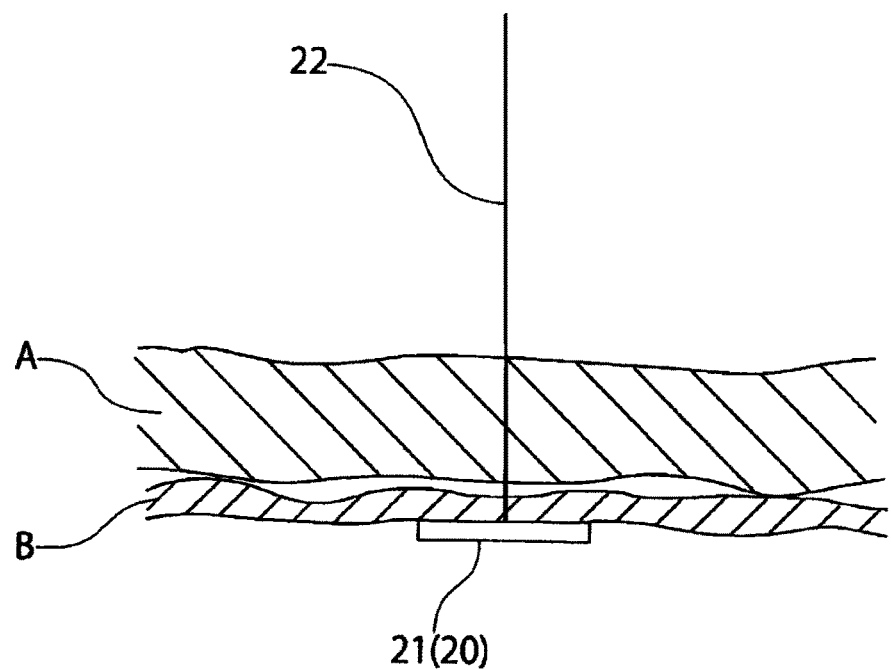
FIG. 10 A sectional view showing a state in which the engaging portion of the organ fixing instrument of the first embodiment of the first aspect is engaged in the interior of the stomach wall.
Figure 11:
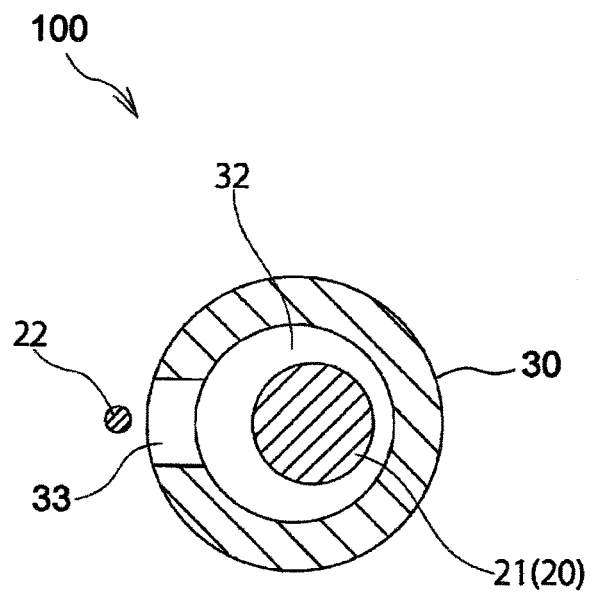
FIG. 11 A sectional view taken along the line A-A of FIG. 1 showing the first embodiment of the first aspect.
Figure 12:
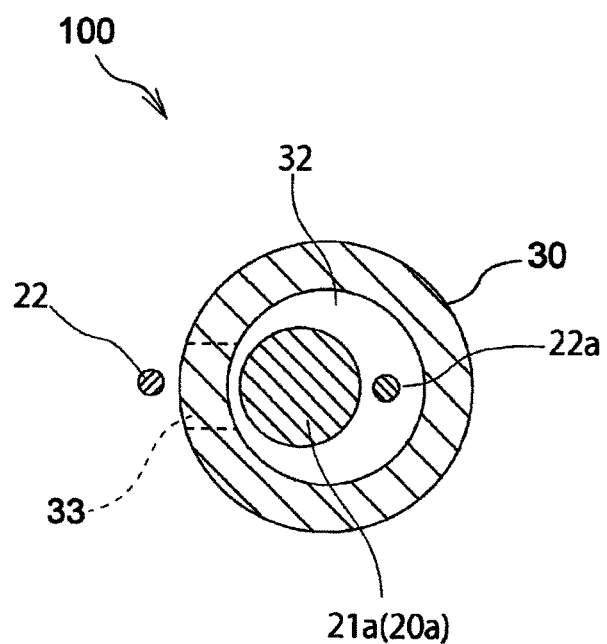
FIG. 12 A sectional view taken along the line B-B of FIG. 1 showing the first embodiment of the first aspect.

FIG. 1 is a partial sectional view showing the organ fixing instrument of the first embodiment of the first aspect of the present invention. FIG. 2 is a schematic perspective view showing the organ fixing instrument. FIG. 3 is a partial side view of the organ fixing instrument. FIG. 4 is a partial perspective view showing the internal mechanism of the organ fixing instrument. FIG. 5 is a side view showing the operating portion. FIG. 6 is an another side view showing the operating portion. FIG. 7 is a side view showing a state in which the engaging claw of the operating portion of the first embodiment is pushed. FIG. 8 is a sectional view showing a state in which the organ fixing instrument is punctured in the abdomen. FIG. 9 is a sectional view showing a state in which the operating portion of the organ fixing instrument comes down. FIG. 10 is a sectional view showing a state in which the engaging portion is engaged in the interior of the stomach wall. FIG. 11 is a sectional view taken along the line A-A of FIG. 1. FIG. 12 is a sectional view taken along the line B-B of FIG. 1.

The organ fixing instrument 100 is provided with the suturing tools 20, 20a, the puncture needle 30, and the extrusion apparatus 40 having the operation unit main body 63, as shown in FIGS. 1 and 2.

The suturing tools 20, 20a comprise the rod-shaped engaging portions 21, 21a and the sutures 22, 22a connected to the engaging portions 21, 21a, as shown in FIG. 1.

The puncture needle 30 can house at least a plurality of engaging portions 21, 21a, for example, it can house two engaging portions in the present embodiment.

The extrusion apparatus 40 is intended to push out a plurality (e.g. two) of engaging portions 21, 21a from the puncture needle 30 one by one by operating the operation unit main body 63.

Based on the above structure, the suturing tools 20, 20a are characterized in that the suture 22a of a part of a plurality (e.g. two) of the engaging portions 21, 21a is inserted into the interior of the puncture needle 30, and the other suture 22 is derived from the inside to the outside of the puncture needle 30 at the side surface of the puncture needle 30 in the axial direction, as shown in FIG. 1. In this specification, the side of the needle point 31 of the puncture needle 30 is referred to as the tip end side, and the side of the puncture needle 30 that is fixed to the extrusion apparatus 40 is referred to the base end side.

Then, the suturing tools 20, 20a of the present embodiment will be described in detail.

A plurality of, for example, two suturing tools 20, 20a are loaded in the organ fixing instrument as shown in FIG. 1, and used as a repeated type.

The suturing tools 20, 20a comprise the side of the needle point 31 of the puncture needle 30, that is to say, the suturing tool 20 of the first stage and the suturing tool 20a of the second stage that is located at the next stage, in order from the tip end side of the puncture needle 30. Hereinafter, the number of stages of the suturing tool means the order in which it was viewed from the tip end side of the puncture needle 30.

The engaging portions 21, 21a are rod-shaped metal illustrated in stainless steel, for example, cylindrical. However, the engaging portions 21, 21a may be made of non-metallic material such as resin.

One end of each of the sutures 22, 22a is heat-sealed or adhesively fixed to the middle of the length (axial direction) of the engaging portions 21, 21a, for example, the central portion or the like of the engaging portion 21, 21a, or fixed around the engaging portion 21, 21a by swaging. The other end of the sutures 22, 22a is derived to the outside of the organ fixing instrument 100 through the internal or external of the puncture needle 30.

Then, the puncture needle 30 of the present embodiment will be described in detail.

The puncture needle 30 is a needle made of stainless steel cylinder, the interior of the puncture needle 30 is a housing portion 32 into which the engaging portions 21, 21a freely insert, as shown in FIG. 1.

The housing portion 32 can house a plurality of, for example, two engaging portions 21, 21a along the axial direction of the puncture needle 30.

The housing portion 32 has one end portion open to the needle tip 31 and the other end portion which communicates with the extrusion apparatus 40.

The housing portion 32 is hollow, and its whole length is set to the length of two pieces of the engaging portions 21, 21a or more.

The inner diameter of the housing portion 32, namely the inner diameter of the puncture needle 30 is the first total length or more in which the minor axis of the engaging portions 21, 21a is added with the minor axis of the sutures 22, 22a, and less than the second total length in which the major axis of the engaging portions 21, 21a is added with the major axis of the two sutures 22, 22a. In addition, it is preferable that the inner diameter of the housing portion 32, namely the inner diameter of the puncture needle 30 is the first total length or more in which the minor axis of the engaging portions 21, 21a is added with the minor axis of the sutures 22, 22a, and less than the third total length in which the first total length is added with the minor axis of the sutures 22, 22a.

In this specification, the major axis is defined as the diameter of an exact circle (circumscribed circle) having minimum diameter which can include a circular shape, ellipsoidal shape, a polygon or the like, which is a cross-sectional shape of the puncture needle 30 or the engaging portion 21, 21a. The minor axis is defined as the diameter of an exact circle (inscribed circle) having maximum diameter which can be included in a circular shape, ellipsoidal shape, a polygon or the like, which is a cross-sectional shape of the puncture needle 30 or the engaging portion 21, 21a. In addition, when the cross-sectional shape of the suture is an exact circular shape, the minor axis and the major axis are read as the diameter of the exact circle. The cross-sectional shape of the puncture needle 30 and the engaging portion 21, 21a is not limited to an exact circle, it may be ellipsoidal shape, a polygon or the like.

In other words, there is a following relationship.

The first total length=the minor axis of the engaging portion+the minor axis of the suture×1(piece)  (1)

The second total length=the major axis of the engaging portion+the major axis of the suture×2 (pieces)  (2)

The first total length=<the inner diameter of the puncture needle<the second total length  (3)

In addition to the above relationship, it is preferable to satisfy the following relationship.

The third total length=the minor axis of the engaging portion+the minor axis of the suture×2 (pieces)  (4)

The first total length=<the inner diameter of the puncture needle<the third total length  (5)

Therefore, according to the organ fixing instrument 100 of the present embodiment, it is possible to thin the outer diameter of the puncture needle 30 in comparison with the instrument of Patent Document 1, in which a plurality of sutures are passed on both sides of the periphery of the engaging portion by facing. For convenience, a state in which the engaging portions 21, 21a and the sutures 22, 22a are loosely inserted into the puncture needle 30 is shown in FIG. 12. However, as described above, the inner diameter of the puncture needle 30 is preferably the first total length or more and less than the second total length, and more preferably the first total length or more and less than the third total length.

The penetrating portion, that is to say, the slit 33 penetrating the inside and outside, through which the suture 22 of the suturing tool 20 of the first stage passes, is provided at the puncture needle 30, as shown in FIG. 1. The penetrating portion is a portion which becomes the path for inserting the suture 22 to the inside and outside of the puncture needle 30, and is formed by penetrating the inside and outside of the lateral of the puncture needle 30 in the axial direction. The penetrating portion may be provided with the slit 33 as the present embodiment, it may comprise a transverse hole (see the third embodiment), and may comprise both.

As shown in FIG. 1, the slit 33 extends toward the operation unit main body 63 from the needle tip 31 of the puncture needle 30. In the slit 33, one end portion is open to the needle tip 31, the other end portion is linearly extending toward the base end side of the puncture needle 30, that is to say, toward the extrusion apparatus 40 along the axial direction of the puncture needle 30, and terminates in the intermediate portion of the puncture needle 30 (the tip end side from the base end side of the puncture needle 30) to form a dead end. The end position of the slit 33, that is to say, the position of the other end portion which is the dead end, is necessary to extend to the placement area of the suture 22 in the first stage of the suturing tool 20 in a state of being housed in the housing portion 32. However, it may extend to the extrusion apparatus 40 side (base end side), longer than this. The groove width of the slit 33 is set to the thickness of one suture 22 or more.

In the present embodiment, since there are two suturing tools 20, 20a, as shown in FIG. 12, one of the sutures 22, 22a, that is to say, the suture 22 of the first stage passes the outside of the puncture needle 30, other one, that is to say, the suture 22a of the second stage of goes through the interior.

Thus, the paths of two sutures 22, 22a are completely different in the form divided to inside and outside of the puncture needle 30, and therefore the sutures never intersect, the entanglement of the two sutures 22, 22a can be completely prevented.

Then, the extrusion apparatus 40 of the present embodiment will be described in detail.

The extrusion apparatus 40 is for performing the repeating type operation.

The extrusion apparatus 40, as shown in FIGS. 2 to 7, when roughly divided, it comprises a cylindrical portion 50, an operation unit 60, a grip portion 70, a locking device 80.

The cylindrical portion 50 is a cylinder made of synthetic resin, as shown in FIGS. 2 to 4, the puncture needle 30 is fixed to the cylinder. The cylindrical portion 50 is open at both ends, the base end portion of the puncture needle 30 which is the opposite side of the needle tip 31 is fixed to one opening end portion, the inside of the cylindrical portion 50 communicates with the housing portion 32 of the puncture needle 30 through this one end portion, and the operation unit 60 is inserted into the opening of the other end.

In addition, the thread exit hole 51 penetrating the inside and outside is provided at the cylindrical portion 50, as shown in FIG. 4. The suture 22a derived to inside of the cylindrical portion 50 through the housing portion 32 of the puncture needle 30 goes through the thread exit hole 51.

The operation unit 60 extrudes the engaging portions 21, 21a housed in the housing portion 32 of the puncture needle 30 from the needle tip 31 of the puncture needle 30 through the interior of the cylindrical portion 50.

The operation unit 60 comprises a push rod 61, a pressing portion 62, and an operation unit main body 63, as shown in FIGS. 2 to 7, when roughly divided.

The push rod 61 is a stainless steel mandrel, as shown in FIGS. 4 and 8, and extrudes the engaging portions 21, 21a housed in the housing portion 32 from the needle tip 31 by being inserted into the housing portion 32 of the puncture needle 30 from the interior of the cylindrical portion 50, and sliding in the housing portion 32. That is to say, since the first stage of the engaging portion 21 and the second stage of the engaging portion 21a positioned at the next stage are accommodated in this order from the needle tip 31, the push rod 61 comes into contact with the second stage of the engaging portion 21a. When the push rod 61 proceeds to the needle tip 31 side (tip end side of the puncture needle 30), the second stage of engaging portion 21a proceeds to the needle tip 31 side by being pushed by the push rod 61. Therefore, the first stage of the engaging portion 21 also proceeds to the needle tip 31 side by being pushed by the second stage of the engaging portion 21a.

The pressing portion 62 is a cylinder made of synthetic resin, as shown in FIG. 4, the push rod 61 is fixed to one end, the other end reaches the operation unit main body 63 described later, and it is intended to transmit the pressure of the operation unit main body 63 to the push rod 61. The pressing portion 62 is slidably held in the cylindrical portion 50, and projects from the opening of the other end at the upper side to the outside of the cylindrical portion 50 of the same figure.

The operation unit main body 63 is a disk-shaped synthetic resin, as shown in FIGS. 4 to 7, it is intended to perform the pressing operation. As shown in FIG. 2, the operation unit main body 63 protrudes into a disc shape from the upper end of the pressing portion 62 located at the upper side in the same figure. The outer diameter of the operation unit main body 63 is set to larger than the inner diameter of the opening of the other end of the cylindrical portion 50 which opens upward in the same figure in order not to be accidentally buried in the cylindrical portion 50.

Then, the gripping portion 70 of the present embodiment will be described in detail.

The gripping portion 70 is a flat plate-shaped synthetic resin and it is intended to grip the extrusion apparatus 40.

As shown in FIG. 2, the gripping portion 70 symmetrically protrudes toward the both of the left and right sides in plates from the lower side of the cylindrical portion 50 in the same figure.

Then, the locking device 80 of the present embodiment will be described in detail.

The locking device 80 regulates the operation unit 60 so as not to inadvertently slide against the cylindrical portion 50.

As shown in FIG. 4, the locking device 80 comprises the engaging claw 81, the recessed portions 82, 82a, when roughly divided. In addition to this, the cylindrical portion 50 is provided with the release buttons 83, 84 for releasing the locked state of the locking device 80.

The engaging claw 81 prevents the pressing of the operation unit 60 to the cylindrical portion 50 by fitting into one of the recessed portions 82, 82a. As shown in FIGS. 4, 6 and 7, the engaging claw 81 is provided at the pressing portion 62 and protrudes from the outer periphery in convex form. The pressing portion 62 is formed in a cylindrical shape, and the outer peripheral wall of both sides of the engaging claw 81 is cut. Thus, the engaging claw 81 of the convex form is possible to elastically deflect to the inside of the cylinder of the pressing portion 62.

As shown in FIG. 4, the recessed portions 82, 82a are provided at the cylindrical portion 50, and are provided at upper and lower two stages in the same figure.

The recessed portions 82, 82a penetrate the inside and outside of the cylindrical portion 50, the engaging claw 81 fits from the inner peripheral side of the cylindrical portion 50, and the release buttons 83, 84 described later are attached on the outer peripheral side, respectively.

In a state in which the engaging claw 81 is fitted into the recessed portion 82 located at the upper side of FIG. 4, as shown in FIG. 8, the tip of the push rod 61 faces the second stage housed within the housing portion 32 of the puncture needle 30, that is to say, the engaging portion 21a which is located at the upper side in the same figure.

In a state in which the engaging claw 81 is fitted into the recessed portion 82 located at the upper side, the operation unit 60 is prevented from further being pushed into the interior of the cylindrical portion 50, and the suturing tools 20, 20a are prevented from being extruded from the needle tip 31 of the puncture needle 30. The operation unit 60 is also restricted from coming out from the inside of the cylindrical portion 50.

When the engaging claw 81 which has been fitted into the recessed portion 82 located at the upper side, proceeds toward the recessed portion 82a located at the lower side in FIG. 4, the second stage of the engaging portion 21a proceeds to the needle tip 31 side by being pushed by the push rod 61. Therefore, the first stage of the engaging portion 21 is pushed out from the needle tip 31 by being pushed by the second stage of the engaging portion 21a.

In this position, the engaging claw 81 is fitted into the recessed portion 82a located at the lower side. In a state in which the engaging claw 81 is fitted into the recessed portion 82a located at the lower side, the operation unit 60 is prevented from further being pushed into the interior of the cylindrical portion 50, the second stage of the suturing tool 20a is prevented from being extruded from the needle tip 31 of the puncture needle 30.

The release buttons 83, 84 are protrusion shape of button type comprising synthetic resin, and the like. As shown in FIG. 4, the release buttons 83, 84 push the engaging claw 81 that fits into one of the recessed portions 82, 82a in the direction from the recessed portions 82, 82a to the inside of the cylindrical portion 50, namely, radially inward toward the center of the cylindrical portion 50. As a result, the engaging claw 81 is disengaged from the recessed portions 82, 82a, and the locking state is released.

As shown in FIG. 4, the release buttons 83, 84 fit into the upper and lower recessed portions 82, 82a from the outer periphery of the cylindrical portion 50, although not shown, and project from the outer circumference by the spring force of the leaf spring or coil spring.

Next, the method for using the organ fixing instrument 100 of the present embodiment will be described by referring to FIGS. 8 to 10.

The organ fixing instrument 100 is used as an initial state of the instrument in which the engaging claw 81 is fitted into the recessed portion 82 located at the upper side in FIG. 4.

As shown in FIG. 8, the puncture needle 30 is punctured from the outside of the patient's body until penetrating the skin side wall A and stomach wall B, thereby exposing the needle tip 31 within the gastric cavity.

Next, as shown in FIG. 9, the release button 83 located at the upper side in the same figure is pressed. When pressing the release button 83, the engaging claw 81 which is fitted into the recessed portion 82 located at the upper side in the same figure is disengaged, and the locked state of the locking device 80 is released.

Then, as shown in FIG. 9, the operation unit main body 63 is pressed toward the inside of the cylindrical portion 50.

When pressing the operation unit main body 63, the push rod 61 is advanced through the housing portion 32 of the puncture needle 30, via the second stage of the engaging portion 21a, the first stage of the engaging portion 21 is pushed out from the needle tip 31.

Therefore, as shown in FIG. 9, the first stage of the engaging portion 21 is introduced into the gastric cavity.

The organ fixing instrument 100 is recovered by pulling out the puncture needle 30 to the outside of the body.

Then, as shown in FIG. 10, by pulling the suture 22 of the first stage of the engaging portion 21 from outside the body, the engaging portion 21 attracts the stomach wall B to the skin side wall A side. Then, the stomach wall B is fixed to the skin side wall A by fixing the suture 22 to the outside of the body.

Then, although not shown, the puncture needle 30 of the recovered organ fixing instrument 100 is punctured from different position of the skin side wall A until penetrating stomach wall B, thereby exposing the needle tip 31 within the stomach.

Then, the release button 84 located at the lower side in FIG. 4 is pressed. When pressing the release button 84, the engaging claw 81 fitted into the recessed portion 82a positioned on the lower side in the same figure, is disengaged, and the locked state of the locking device 80 is released.

Then, the operation unit main body 63 is pressed toward the inside of the cylindrical portion 50.

When pressing the operation unit main body 63, the push rod 61 is advanced through the housing portion 32 of the puncture needle 30, and the second stage of the engaging portion 21a is pushed out from the needle tip 31.

Therefore, the second stage of the engaging portion 21a is introduced into the gastric cavity.

Similarly to the first stage of the suture 22, by pulling and fixing the suture 22a of the second stage of the engaging portion 21a from outside the body, the stomach wall B is fixed to the skin side wall A.

Second Embodiment

Figure 13:
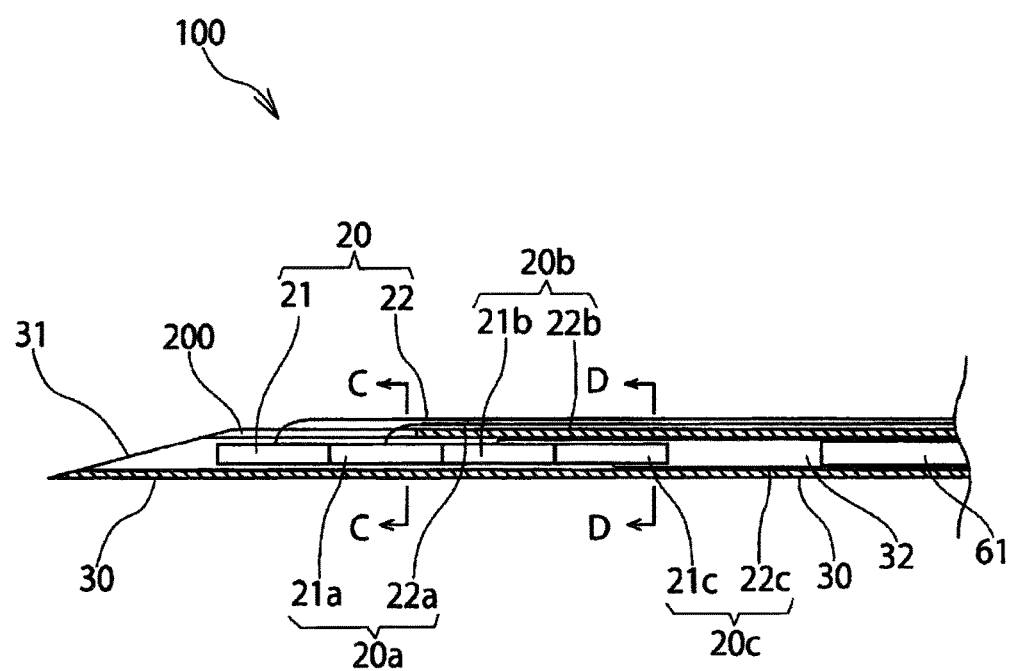
FIG. 13 A partial sectional view showing the organ fixing instrument of the second embodiment of the first aspect of the present invention.
Figure 14:
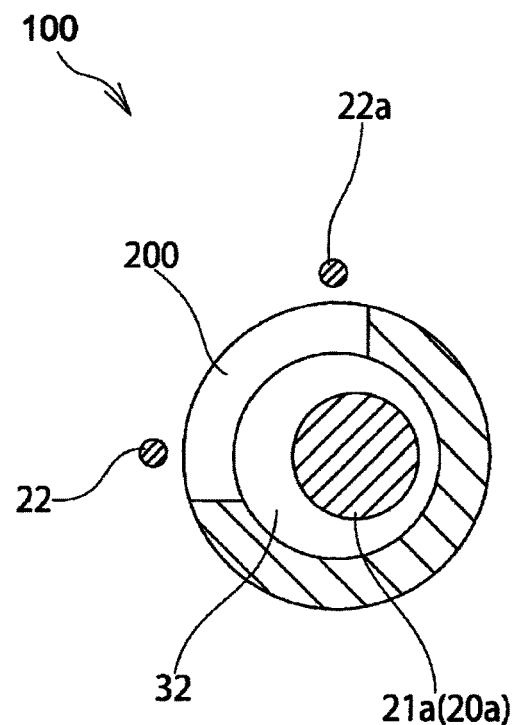
FIG. 14 A sectional view taken along the line C-C of FIG. 13 showing the second embodiment of the first aspect.
Figure 15:
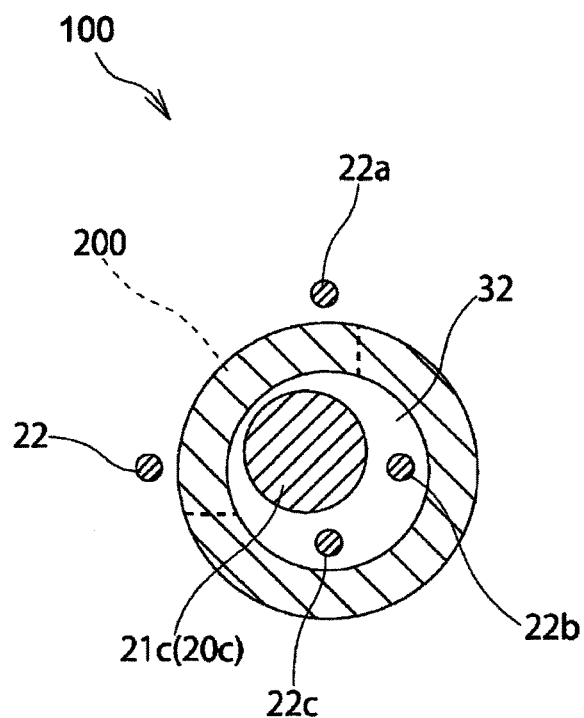
FIG. 15 A sectional view taken along the line D-D of FIG. 13 showing the second embodiment of the first aspect.

FIG. 13 is a partial sectional view showing the organ fixing instrument of the second embodiment of the first aspect of the present invention. FIG. 14 is a sectional view taken along the line C-C of FIG. 13. FIG. 15 is a sectional view taken along the line D-D of FIG. 13.

First, the organ fixing instrument 100 of the present embodiment differs from the first embodiment in that the number of suturing tools 20, 20a to 20c is increased.

Second, the organ fixing instrument 100 of this embodiment differs from the first embodiment in that the slit 200 is extended.

As shown in FIG. 13, four or more (four in this embodiment) of the suturing tools 20, 20a to 20c are loaded. That is to say, four engaging portions 21, 21a to 21c are accommodated in the housing portion 32 of the puncture needle 30.

Among four or more (four in this embodiment) of the sutures 22, 22a to 22c, the sutures 22, 22a of the two suturing tools 20, 20a are derived from the inside to the outside of the puncture needle 30.

That is to say, among the four sutures 22, 22a to 22c of the present embodiment, two first stage, second stage of sutures 22, 22a pass outside of the puncture needle 30, and the remaining two sutures, i.e. the third stage, fourth stage of the sutures 22b, 22c pass through the interior of the puncture needle 30 (housing portion 32). Adjacent sutures 22, 22a to 22c are spaced apart in the outer circumferential direction of the puncture needle 30, and are arranged at regular intervals, i.e. at 90 degree intervals.

Assuming that the suturing tools 20, 20a to 20c is 3 or more (four in the present embodiment), the slit 200 extends from the placement region of the engaging portion 21 located at the tip end side of the puncture needle 30 (first stage) to at least the middle of the placement region of the engaging portion 21a located at the next stage (second stage). In addition to the suture 22 of the engaging portion 21 located at the tip end side of the puncture needle 30 (first stage), the slit 200 of the present embodiment enables that the suture 22a of the engaging portion 21a located at the next stage (second stage) is inserted. That is to say, the suture 22 of the first stage of the engaging portions 21 and the suture 22a of the second stage of the engaging portion 21a which are loaded into the puncture needle 30 are drawn to the outside through the slit 200.

The slit 200 is formed as one end is open to the needle tip 31 and the other end linearly extends along the axial direction of the puncture needle 30, to the base end side of the puncture needle 30, that is to say, to the extrusion apparatus 40 side, and the other end is a dead end. The position of the dead end of the other end is necessary to extend to the placement area of the suture 22a of the second stage of the suturing tool 20a in a state of being housed in the housing portion 32. However, it may extend to the base end side of the puncture needle 30 (extrusion apparatus 40 side), longer than this. With regard to the slit 200, a wide opening may form along the outer periphery of the puncture needle 30. For example, in FIG. 14, the slit 200 is formed as about ¼ of the opening of the outer periphery of the puncture needle 30. In the configuration of FIG. 14, the first stage of the suture 22 is derived from the inside of the housing portion 32 to the outside of the puncture needle 30 along one end of the opening in the circumferential direction of the slit 200, and the second stage of the suture 22a is derived from the inside of the housing portion 32 to the outside of the puncture needle 30 along the other end in the circumferential direction of the puncture needle 30. Thus, the phases of the first stage of the suture 22 and the second stage of the suture 22a is made different by about 90 degrees, the suture 22 and the suture 22a can be derived to the outside of the puncture needle 30 in a state of being separated, and it is possible to reduce the entanglement of the sutures.

Third Embodiment

Figure 16:
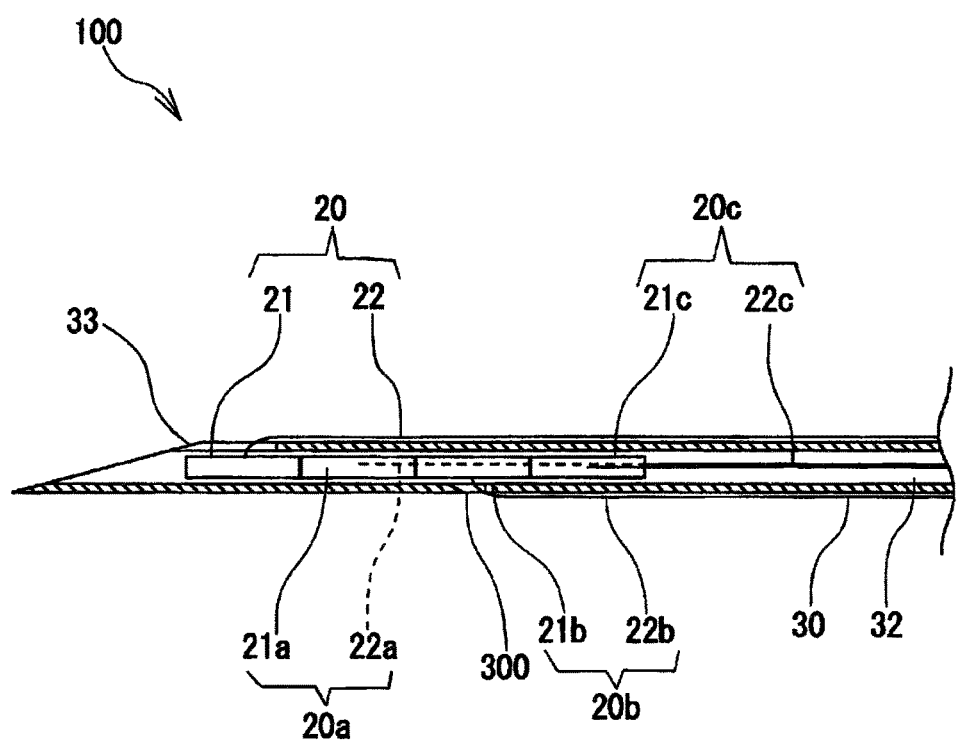
FIG. 16 A partial sectional view showing the organ fixing instrument of the third embodiment of the first aspect of the present invention.
Figure 17:
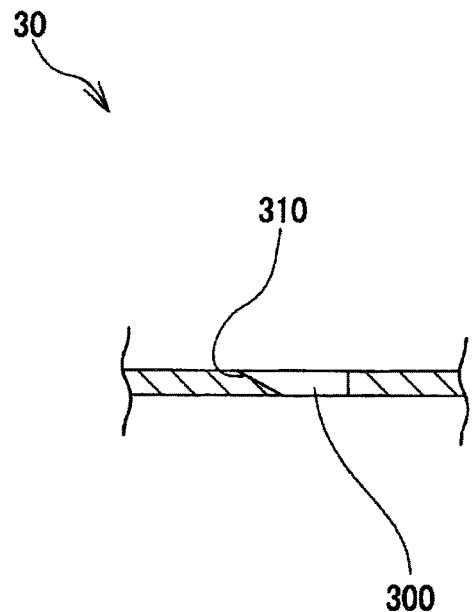
FIG. 17 A partially enlarged sectional view showing the puncture needle of the third embodiment of the first aspect.
Figure 18:
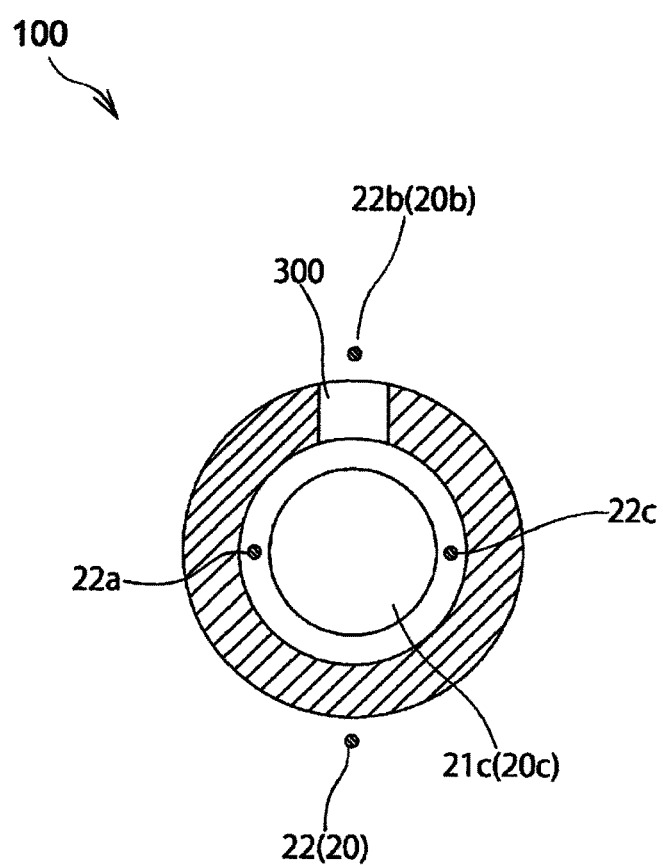
FIG. 18 A sectional view showing the organ fixing instrument of the third embodiment of the first aspect.

FIG. 16 is a partial sectional view showing the organ fixing instrument of the third embodiment of the first aspect of the present invention. FIG. 17 is a partially enlarged sectional view showing the puncture needle. FIG. 18 is a sectional view showing the puncture needle.

First, similarly to the second embodiment, the organ fixing instrument 100 of the present embodiment differs from the first embodiment in that the number of the suturing tools 20, 20a to 20c is increased.

Second, the organ fixing instrument 100 of the present embodiment differs from the first and second embodiments in that the traverse hole 300 is provided as the penetrating portion.

In the present embodiment, similarly to the second embodiment, as shown in FIG. 16, the four suturing tools 20, 20a to 20c are loaded. That is to say, four engaging portions 21, 21a to 21c are accommodated in the housing portion 32 of the puncture needle 30.

The traverse hole 300 penetrating inside and outside is provided at the puncture needle 30.

By any of the sutures 22, 22a to 22c of the engaging portions 21, 21a to 21c accommodated in the housing portion 32 is derived to the outside of the puncture needle 30 through the traverse hole 300, the transverse hole 300 functions as the penetrating portion.

In FIG. 16, one circular traverse hole 300 is formed in side view, and its internal diameter is set to the thickness of the suture 22b or more. The traverse hole 300 is located at the arrangement area of the third stage of the suturing tool 20b which is housed in the housing portion 32, and the suture 22b is derived to the outside of the puncture needle 30 through the hole.

As shown in FIG. 17, end face of the tip end of the traverse hole 300 is inclined toward the inner tip end direction (as it goes from the inside to the outside, as directed to the base end direction from the tip end direction). That is to say, the inclined portion 310 is formed at the end face of the tip end side of the transverse hole 300, and the surface of the inclined portion 310 is formed so as to face the inside (lumen) of the puncture needle 30. The inclined portion 310 reduces the frictional resistance by sliding contact with the third stage of the suture 22b. In other words, when the third stage of the engaging portion 21b which is housed in the housing portion 32 proceeds to the needle tip 31 side of the puncture needle 30, the suture 22b slides contact with the inclined portion 310.

As shown in FIG. 18, the sutures 22, 22b of the two suturing tools 20, 20b that are derived from the inside of the puncture needle 30 to the outside, are opposed to positions across the puncture needle 30. The traverse hole 300 is made different from the slit 33 by 180 degrees in phase, that is, they are arranged to face each other across the puncture needle 30.

As shown in FIG. 16, the suture 22 of the first stage of the engaging portion 21 is derived from the inside of the puncture needle 30 to the outside through the slit 33. The suture 22b of the third stage of the engaging portion 21b is derived from the inside of the puncture needle 30 to the outside through the traverse hole 300. In this case, the first stage of the suture 22 and the third stage of the suture 22b have opposed positions across the puncture needle 30, since the phase of the slit 33 and the traverse hole 300 are different by 180 degrees in the circumferential direction of the puncture needle 30.

Fourth Embodiment

Figure 19:
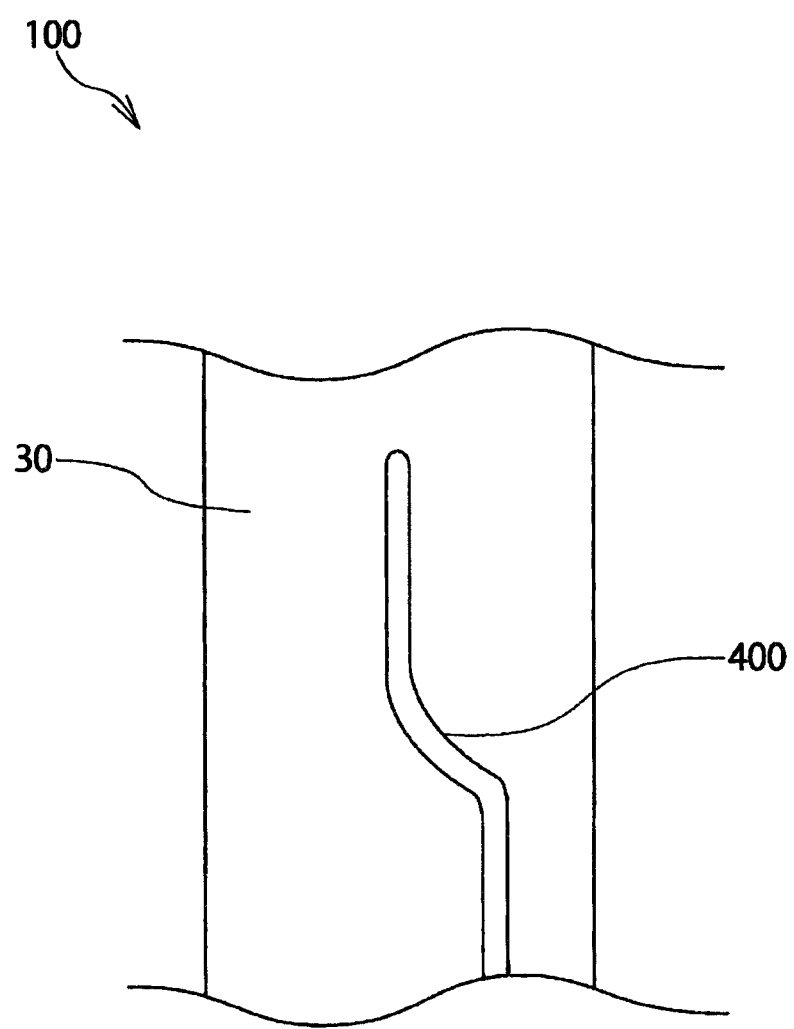
FIG. 19 A partial side view of the puncture needle of the fourth embodiment of the first aspect of the present invention.

FIG. 19 is a partial side view of the organ fixing instrument of the fourth embodiment of the first aspect of the present invention.

The organ fixing instrument 100 of the present embodiment is different from the first and second embodiments in that the slit 400 is formed at the surface of the puncture needle 30 in the non-linear form with respect to the axis.

The slit 400 is a modification of the extended slit 200 as shown in FIGS. 13 and 14 of the second embodiment. Assuming that the number of the suturing tools 20, 20a to 20c is three or more, for example, four, as with the slit 200, as shown in FIG. 19, the slit 400 is non-linearly formed.

Although not shown, one end of the slit 400 is open to the needle tip, as shown in FIG. 19, and the other end extends in the axial direction of puncturing needle 30, that is to say, the other end linearly extends partway upward in the same figure. After that, the other end of the slit 400 is bent in an arc shape, further extends linearly upward, and forms a dead end. That is to say, the slit 400, which has two straight line slits having a straight line in the axial direction and spaced from each other and a slit for communicating the two straight line slits, is formed by integrating these slits.

The position of the other end of the dead end is the same as the slit 200 of the second embodiment. When described with reference to FIG. 13, it is necessary to extend to the arrangement area of the suture 22a of the second stage of the suturing tool 20a in a state of being housed in the housing portion 32. However, it may extend to the extrusion apparatus 40 side, longer than this.

The slit 400 may be formed in a spiral shape in the circumferential direction of the puncture needle 30. Similarly to the slit 200 of the second embodiment, by the midstream of the length is formed in a spiral shape, the first stage of the suture 22 and the second stage of the suture 22a are made different by 90 degree in phase, and they can be derived to the outside of the puncture needle 30 as shown in FIG. 13.

Fifth Embodiment

Figure 20:
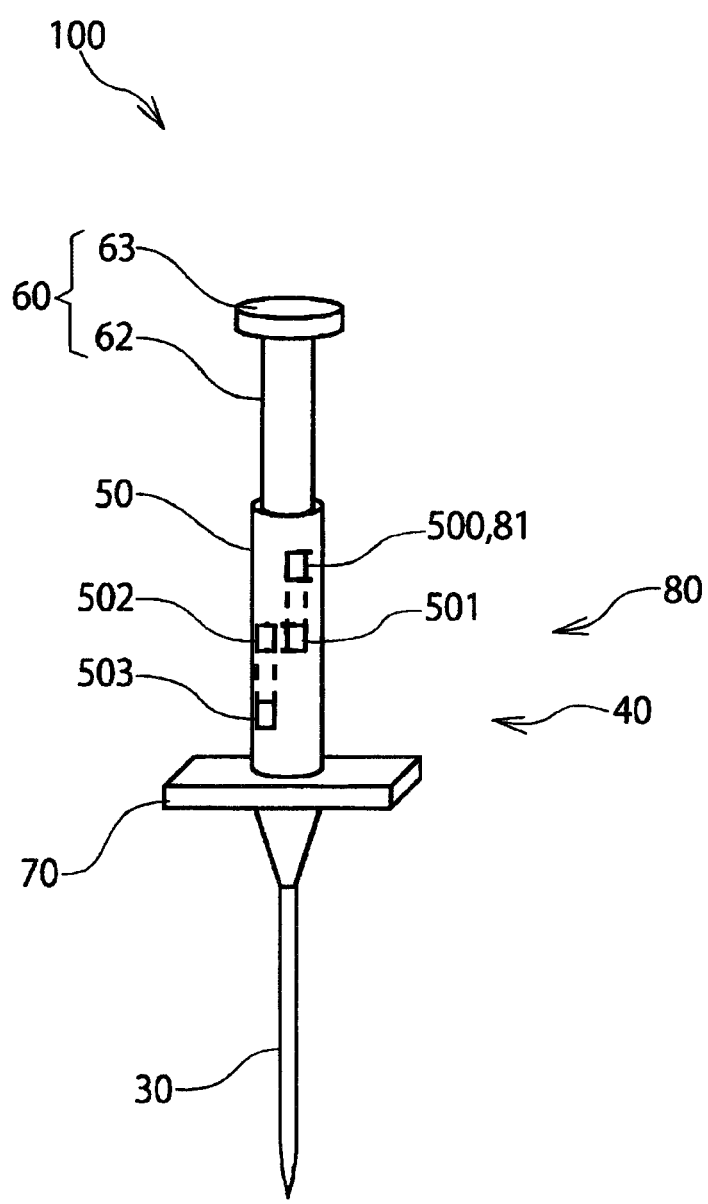
FIG. 20 A schematic perspective view of the organ fixing instrument of the fourth embodiment of the first aspect of the present invention.

FIG. 20 is a schematic perspective view showing the organ fixing instrument 100 of the fourth embodiment of the first aspect of the present invention.

The organ fixing instrument 100 of the present embodiment is different from the first embodiment in that the number of the recessed portions 500 to 503 is increased, and they are disposed at different positions in the circumferential direction of the cylindrical portion 50.

The recessed portions 500 to 503 penetrate inside and outside of the cylindrical portion 50, and the engaging claw 81 of the operation unit 60 is fitted into these recessed portions. The engaging claw 81 has a structure similar to that of the first embodiment described above with reference to FIGS. 5 to 7, and a part of the convex is fitted into any one of the recessed portions 500 to 503, in this case, the part protrudes from the outer periphery of the cylindrical portion 50 in a manner which enables pressing operation.

Similar to that of the first embodiment described above with reference to FIG. 1, assuming that two suturing tools 20, 20a are loaded, the total of four recessed portions 500 to 503 are formed.

Among the four recessed portions 500 to 503, two first, second recessed portions 500, 501 are spaced apart up and down in FIG. 20. The spacing between the first, second recessed portions 500, 501 is matched to the stroke required to push out the first stage of the engaging portion 21 located at the needle tip 31 side, when described with reference to FIG. 1.

Among the four recessed portions 500 to 503, remaining two third and fourth recessed portions 502, 503 shift in the outer circumferential direction of the cylindrical portion 50, and are spaced apart up and down in FIG. 20. Among the third and fourth recessed portions 502, 503, the third recessed portion 502 located at the upper side in FIG. 20, is located at the same height as the second recessed portion 501 located at the lower side. The fourth recessed portion 503 located at the lower side is located away downward from the third recessed portion 502. The distance between the third and fourth recessed portions 502, 503 is matched to the stroke required to push out the second stage of the engaging portion 21a, when described with reference to FIG. 1.

Next, by referring to FIG. 20, the method of using the organ fixing instrument 100 of the present embodiment will be described.

First, the engaging claw 81 of the operation unit 60 fits into the second recessed portion 501 located at the lower side of FIG. 20 when the operation unit 60 is pushed down while pushing the engaging claw 81 from a state fitted into the first recessed portion 500. In this case, when described with reference to FIG. 1, the first stage of the engaging portion 21 is pushed out from needle tip 31.

In addition, when the operation unit 60 is tried to be further pushed down, depression of the operating unit 60 is prevented since the engaging claw 81 is fitted into the second recessed portion 501.

Next, when described with reference to FIG. 1, when the first stage of the engaging portion 21 is pushed out from the needle tip 31, the operation unit 60 is rotated relative to the cylindrical portion 50 while pushing the engaging claw 81 fitted into the second recessed portion 501.

When rotating the operation unit 60, the engaging claw 81 is moved from the second recessed portion 501 to the third recessed portion 502 and fits into the third recessed portion 502.

Then, while pushing the engaging claw 81 fitted into the third recessed portion 502, when pushing down the operation unit 60, the engaging claw 81 fits into the fourth recessed portion 503 located at the lower side of FIG. 20. In this case, when described with reference to FIG. 1, the second stage of the engaging portion 21a is pushed out from needle tip 31.

It should be noted that the present invention is not limited to the embodiments described above, the present invention includes aspects of various modifications and improvements or the like as long as the object of the present invention is achieved.

For example, in the above first embodiment, the engaging portions 21, 21a are cylindrical, they may be hollow cylindrical or cross-sectional shape is not limited to a circle, it may be polygonal.

In addition, in the above first embodiment, although each one suture 22, 22a is used for the engaging portions 21, 21a, plural sutures, and two sutures may be used. In the first embodiment, although the sutures 22, 22a are fixed to the center of the engaging portions 21, 21a, they may be fixed to one end of the engaging portions 21, 21a, and it is possible that a loop of one suture is formed and the both ends are fixed to the both ends of the engaging portions 21, 21a, respectively.

For example, in the first embodiment, although the first stage of the suture 22 passes outside of the puncture needle 30 and the second stage of the suture 22a passes through inside, it is possible that the first stage of the suture 22 passes through inside of the puncture needle 30 and the second stage of the suture 22a passes outside.

For example, in the first embodiment, although the operation unit main body 63 is formed in a disc form, it may be formed into a rod shape.

For example, in the first embodiment, although the grip portion 70 is formed in a flat plate shape, it may be formed in a ring shape or a lever shape. Furthermore, the grip portion 70 may be integrally formed with the cylindrical portion 50 and it may have a separate structure.

For example, although the first embodiment has two suturing tools 20, 20a and the second embodiment has four suturing tools 20, 20a to 20c, the number of the suturing tools may be three or five or more.

For example, in the second embodiment, among the four sutures 22, 22a to 22c, the first stage, the second stage of the two sutures 22, 22a pass outside of the puncture needle 30, and remaining two, namely the third stage, the fourth stage of the sutures 22b, 22c pass through the inside. Instead of this, the first stage, the third stage of the sutures 22, 22b may pass outside, and the second stage, the fourth stage of the sutures 22a, 22c may pass through the inside. Furthermore, the first stage, the fourth stage of the sutures 22, 22c may pass outside of the puncture needle 30, and the second stage, the third stage of the sutures 22a, 22b may pass through the inside. In addition, in the second embodiment, although the adjacent sutures 22, 22a to 22c are arranged at 90 degree intervals, not limited to this, the adjacent sutures 22, 22a to 22c may be arranged each other at 180 degree intervals at facing position across the puncture needle 30.

For example, in the second embodiment, in a case where only three suturing tools 20, 20a to 20b are used instead of the four suturing tools 20, 20a to 20c, among the three sutures 22, 22a to 22b, two sutures may pass the outside of the puncture needle 30 and the remaining one suture may pass through the inside of the puncture needle 30; two sutures may pass through the inside of the puncture needle 30 and remaining one suture may pass the outside of the puncture needle 30. However, it is preferable that two sutures pass the outside of the puncture needle 30 and the remaining one suture pass through the inside of the puncture needle 30.

In the above third embodiment, although the slit 33 and the traverse hole 300 are provided as penetrating portions, it is possible to omit the slit 33 and to form only the traverse hole 300. In addition, a plurality of traverse holes 300 may be provided. Furthermore, traverse hole 300 may be formed to may be formed in shape of ellipse, oval or polygon, in addition to the illustrated circular form in side view.

In the third embodiment, the transverse hole 300 and the slit 33 are arranged at 180 degrees difference in phase. However, it is not limited to 180 degrees, in the sense that the sutures 22, 22a to 22c are hardly entangled.

In the above first to fifth embodiments, as shown in the sixth embodiment of the second aspect described later, the relative rotation about the axis of the adjacent engaging portions may be regulated by forming a concave-convex portion fitted to each other on the end faces of the two adjacent engaging portions.

The above embodiments include the following technical ideas.

(1) A repeated type organ fixing instrument having a plurality of suturing tools comprising a rod-shaped engaging portion, a suture fixed to the engaging portion, a puncture needle for housing a plurality of the engaging portions, wherein the plurality of the engaging portions are extruded one by one from the puncture needle by the operation of a operation unit main body, wherein the suture fixed to at least one of the plurality of engaging portions is inserted within the inside of the puncture needle and wherein the other suture is derived from the inside to the outside of the puncture needle.

(2) The repeated type organ fixing instrument according to (1), wherein a penetrating portion which penetrates inside and outside of the puncture needle, and through which the other suture passes is provided.

(3) The repeated type organ fixing instrument according to (2), wherein the penetrating portion has a slit extending toward the operation unit main body from a needle tip which is the tip of the puncture needle.

(4) The repeated type organ fixing instrument according to any one of (1) to (3), wherein the instrument has two suturing tools, one suture passes outside of the puncture needle, and the other one suture passes through inside of the puncture needle.

(5) The repeated type organ fixing instrument according to (4), wherein an inner diameter of the puncture needle is a first total length or more, in which a minor axis of the engaging portion is added with a minor axis of the suture, and less than a second total length in which a major axis of the engaging portion is added with major axes of the two sutures.

(6) The repeated type organ fixing instrument according to (3), wherein the instrument has three or more suturing tools, the slit extends from an arrangement region of the engaging portion located at the tip end side of the puncture needle to at least a middle of an arrangement region of the engaging portion located at a next stage of the base end side of the puncture needle, and wherein the suture of the engaging portion located at the next stage is inserted into the slit.

(7) The repeated type organ fixing instrument according to (6), wherein the slit is formed in a spiral shape.
(8) The repeated type organ fixing instrument according to any one of (1) to (3), (6) and (7), wherein the instrument has three or more suturing tools, the sutures of the two suturing tools among three or more sutures, are derived from the inside to the outside of the puncture needle, and wherein the sutures are opposed with respect to the puncture needle.
(9) The repeated type organ fixing instrument according to any one of (2), (3), (6), (7) and (8) which is according to (2), wherein the instrument has a transverse hole penetrating inside and outside of the puncture needle as the penetrating portion.
(10) The repeated type organ fixing instrument according to (9), wherein an end face of a tip end side of the traverse hole is inclined from a tip end direction to a base end direction as the end face goes from the inside to the outside.

Second Aspect

The embodiments of the second aspect of the present invention will be described below with reference to the figures. In the figures, the same reference numerals are given to the same components, and the duplicate description may be omitted.

First Embodiment

Figure 21:
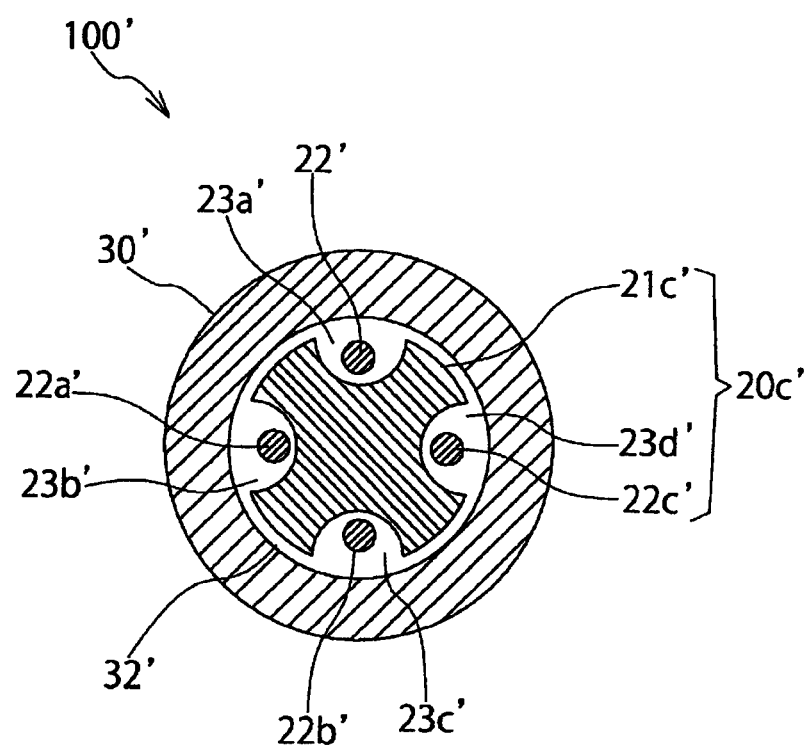
FIG. 21 A sectional view showing the organ fixing instrument of the first embodiment of the second aspect of the present invention.
Figure 22:
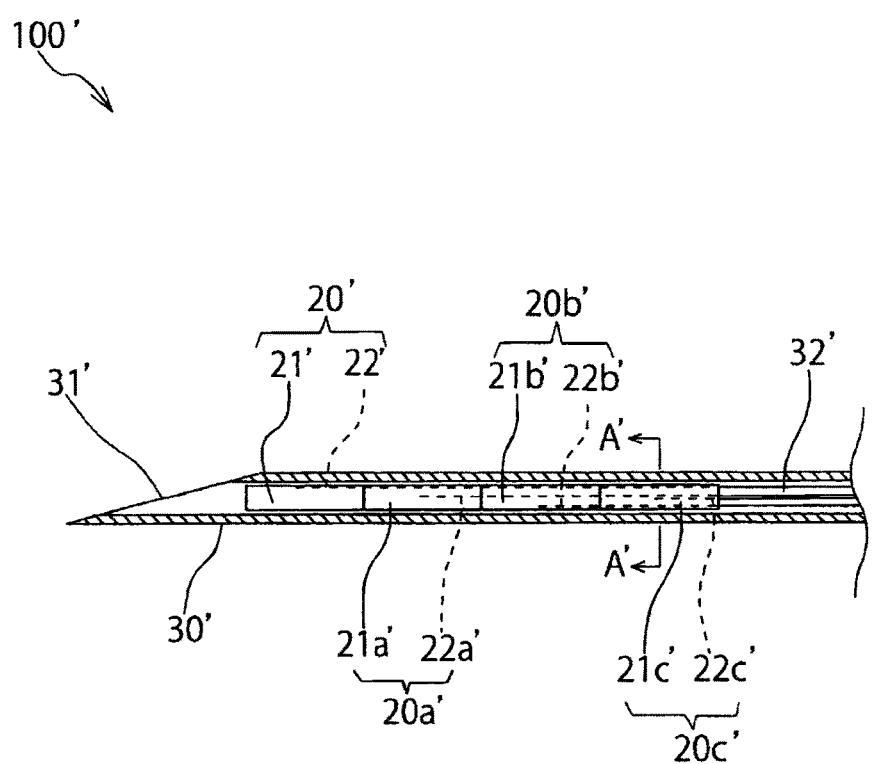
FIG. 22 A partial sectional view showing the organ fixing instrument of the first embodiment of the second aspect.
Figure 23:
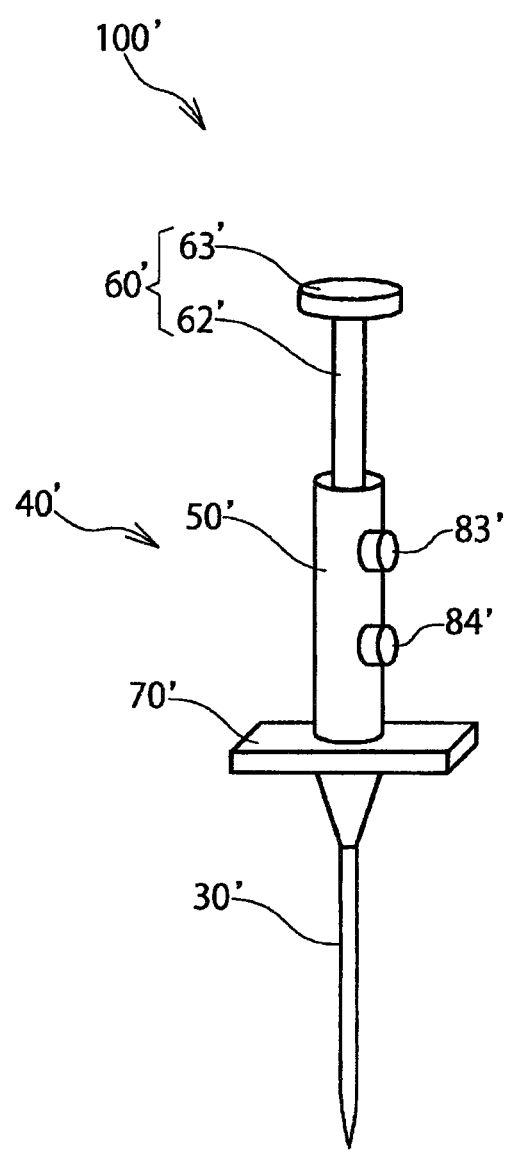
FIG. 23 A schematic perspective view showing the organ fixing instrument of the first embodiment of the second aspect.
Figure 24:
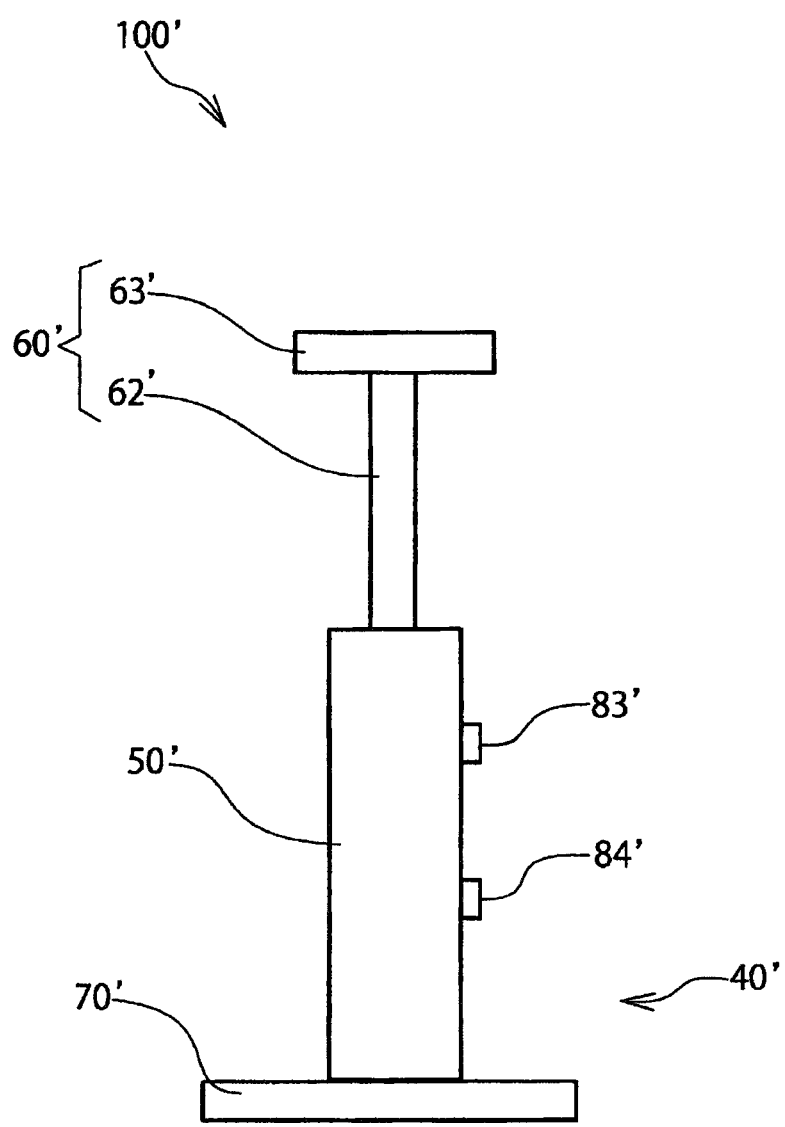
FIG. 24 A partial side view of the organ fixing instrument of the first embodiment of the second aspect.
Figure 25:
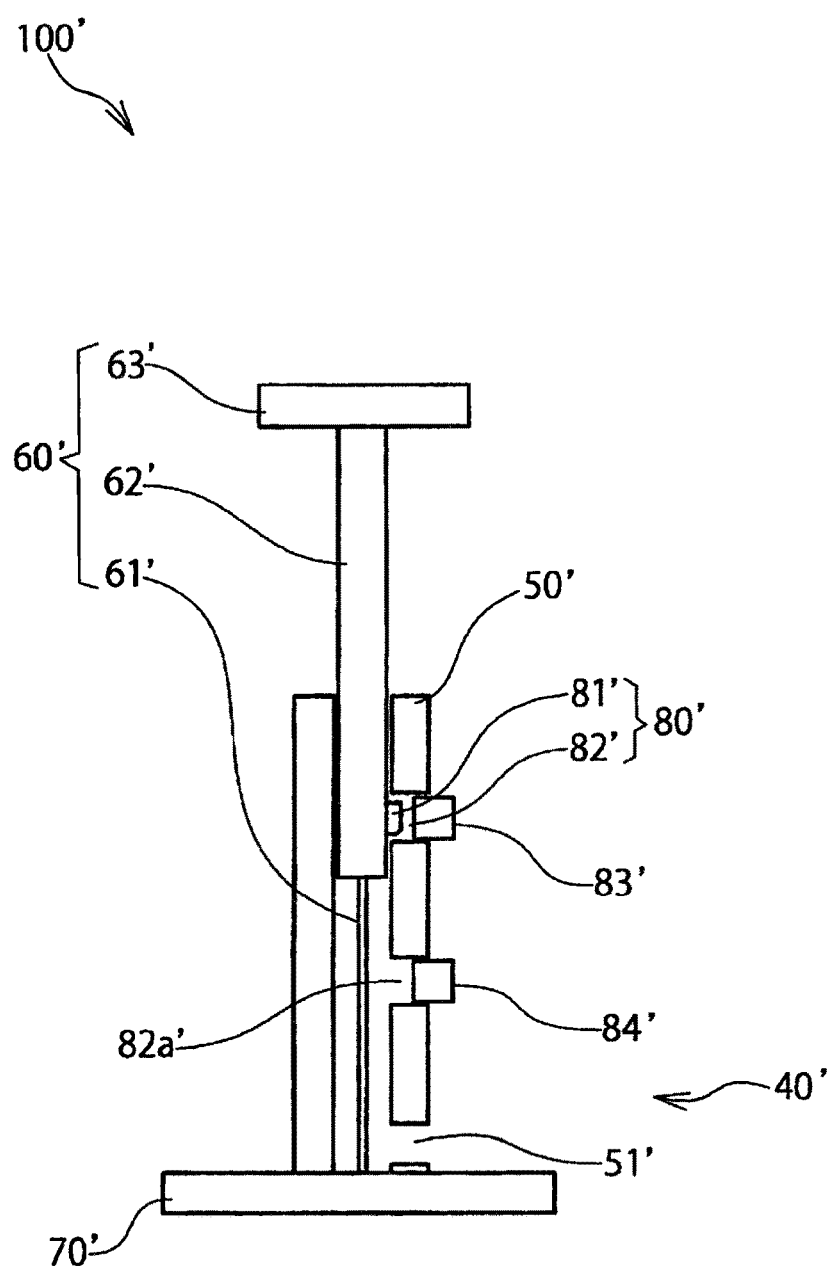
FIG. 25 A partial perspective view showing the internal mechanism of the organ fixing instrument of the first embodiment of the second aspect.
Figure 26:
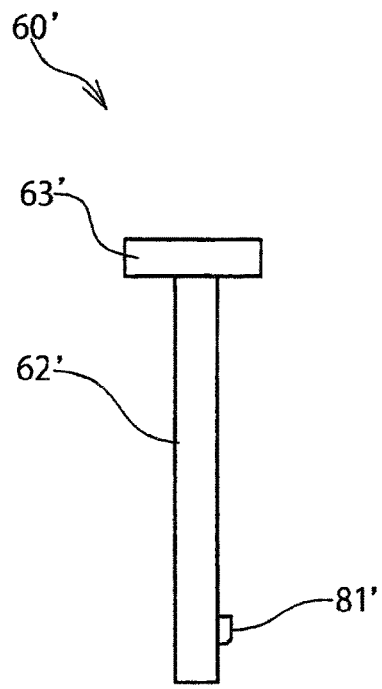
FIG. 26 A side view showing the operating portion of the first embodiment of the second aspect.
Figure 27:
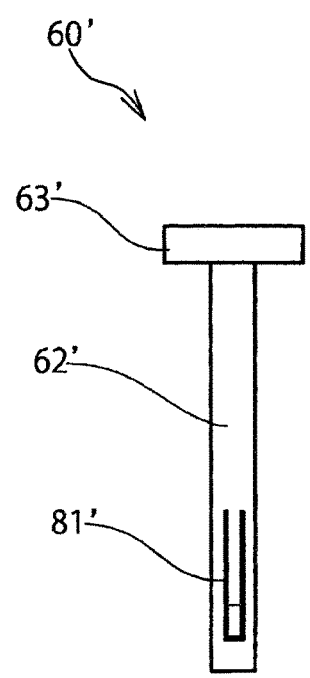
FIG. 27 Another side view showing the operating portion of the first embodiment of the second aspect.
Figure 28:
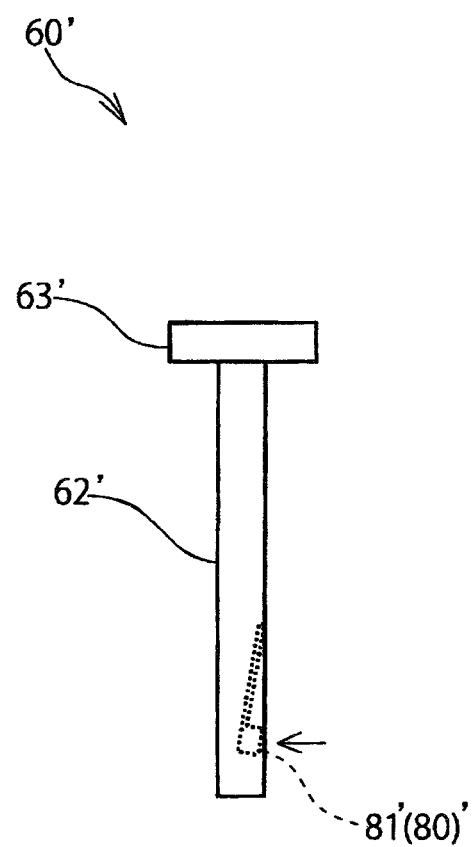
FIG. 28 A side view showing a state in which the engaging claw of the operating portion of the first embodiment of the second aspect is pushed.
Figure 29:
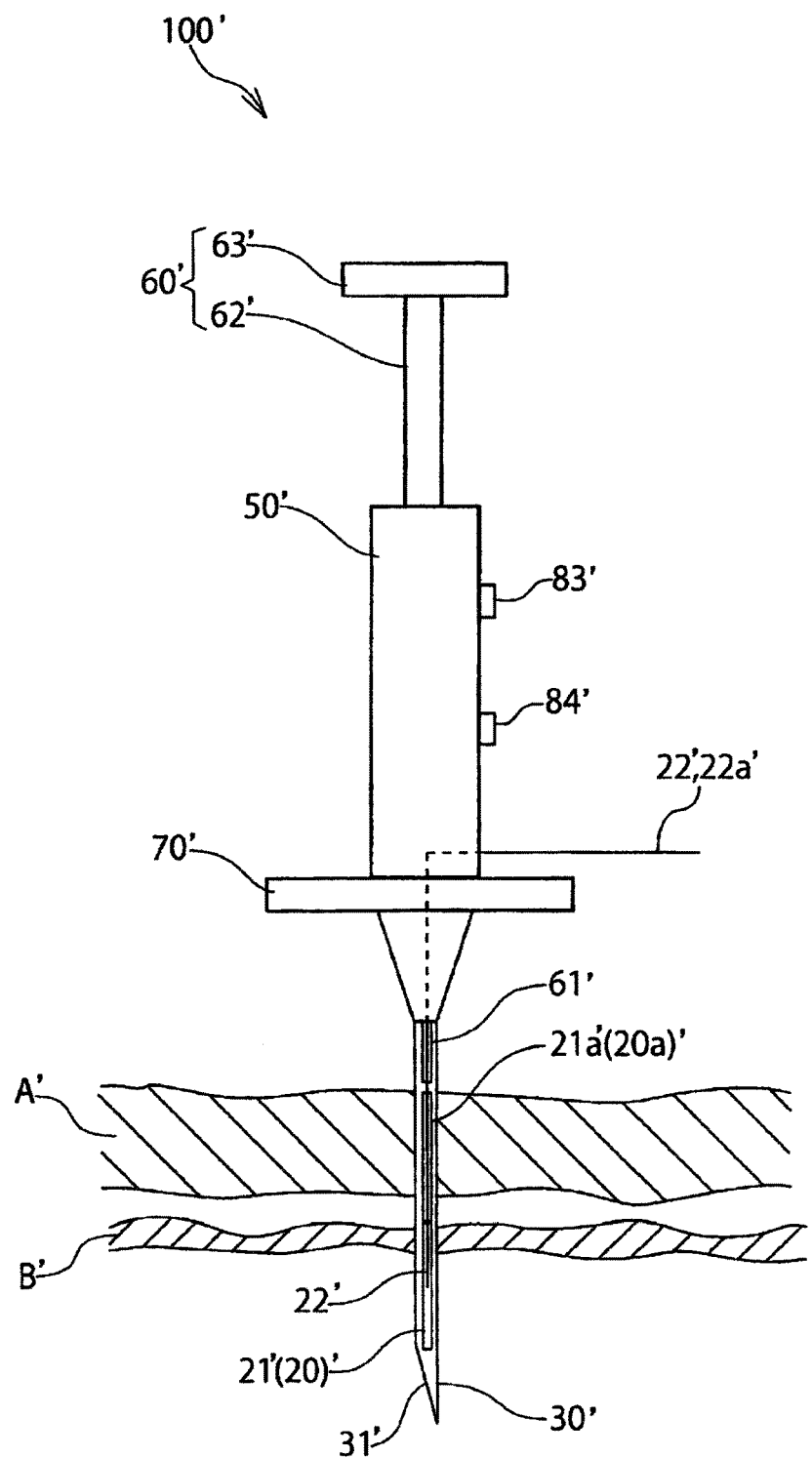
FIG. 29 A sectional view showing a state in which the organ fixing instrument of the first embodiment of the second aspect is punctured in the abdomen.
Figure 30:
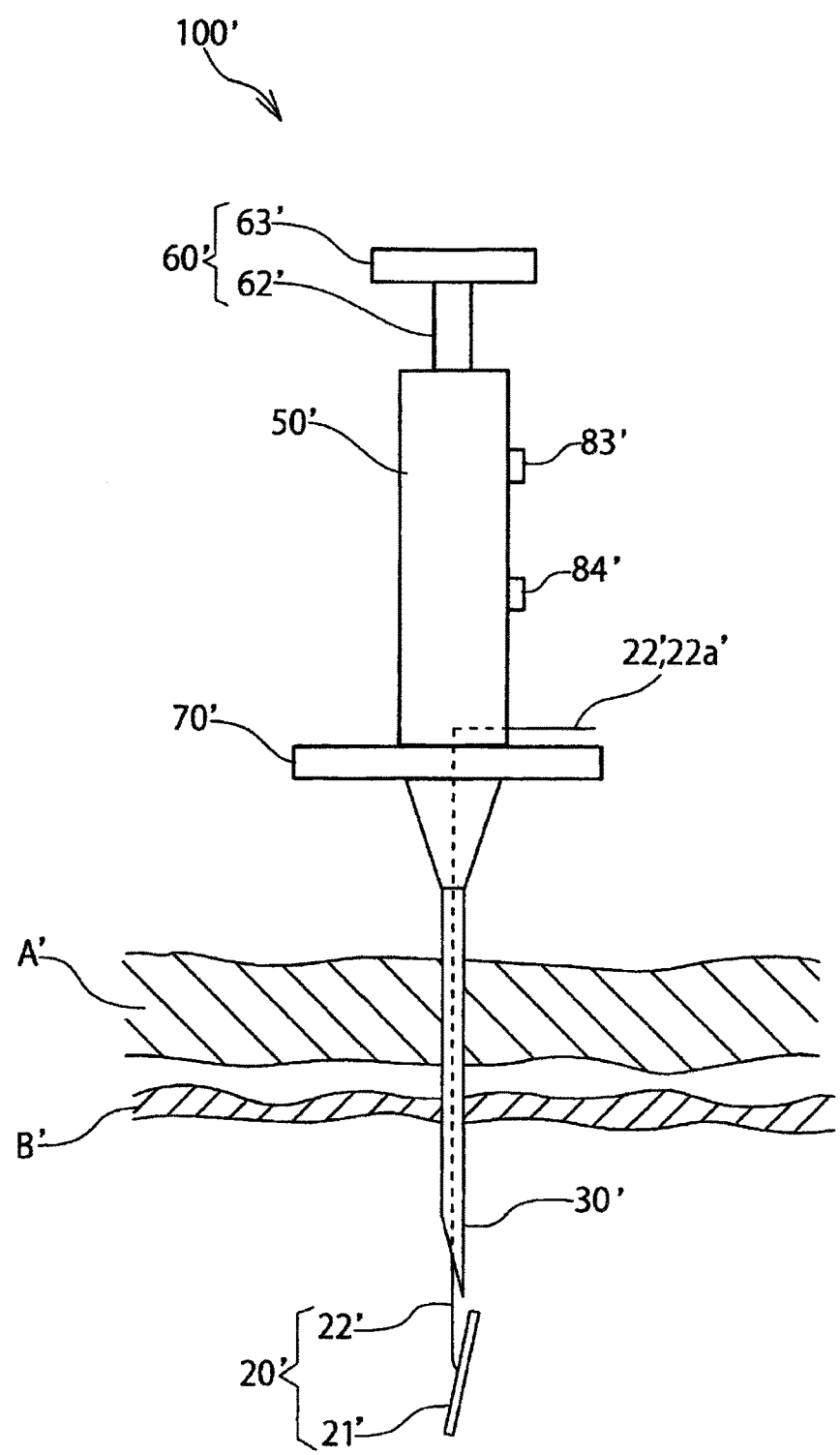
FIG. 30 A sectional view showing a state in which the operating portion of the organ fixing instrument of the first embodiment of the second aspect comes down.
Figure 31:
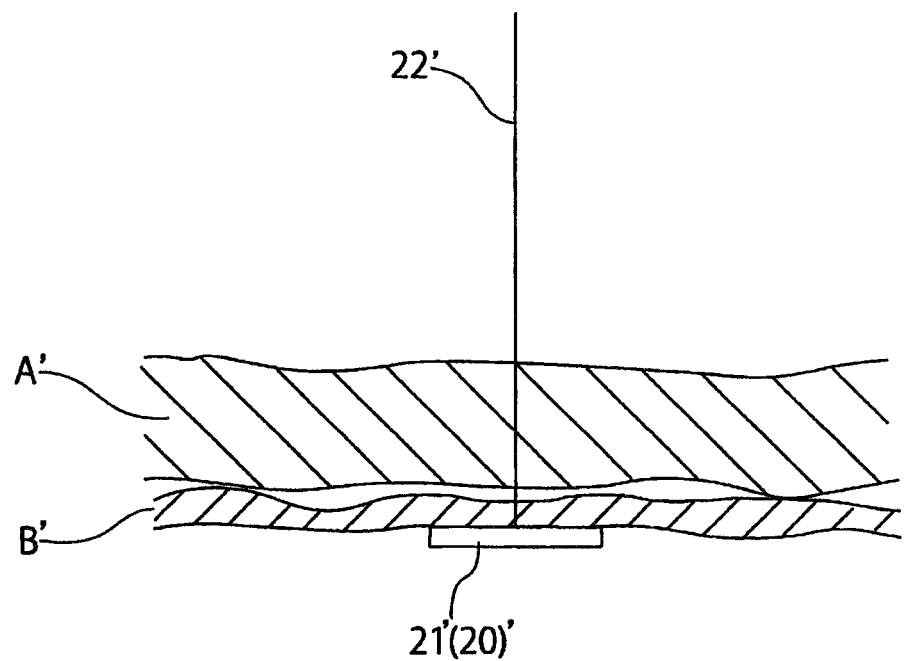
FIG. 31 A sectional view showing a state in which the engaging portion of the organ fixing instrument of the first embodiment of the second aspect is engaged in the interior of the stomach wall.

FIG. 21 shows the organ fixing instrument of the first embodiment of the second aspect of the present invention. FIG. 21 is a sectional view taken along the A'-A' line in FIG. 22. FIG. 22 is a partial sectional view showing the organ fixing instrument. FIG. 23 is a schematic perspective view showing the organ fixing instrument. FIG. 24 is partial side view of the organ fixing instrument. FIG. 25 is a partial perspective view showing the internal mechanism of the organ fixing instrument. FIG. 26 is a side view showing the operation unit. FIG. 27 is another side view showing the operation unit. FIG. 28 is a side view showing a state in which the engagement claw of the operation unit is pushed. FIG. 29 is a sectional view showing a state in which the organ fixing instrument is punctured in the abdomen. FIG. 30 is a sectional view showing a state in which the operation unit of the organ fixing instrument is lowered. FIG. 31 is a sectional view showing a state in which the engaging portion is engaged in the interior of the stomach wall.

As shown in FIGS. 21 to 23, the organ fixing instrument 100' comprises the suturing tools 20', 20a' to 20c', the puncture needle 30', and the extrusion apparatus 40' having the operation unit main body 63'.

As shown in FIGS. 21 and 22, the suturing tools 20', 20a' to 20c' comprises rod-shaped engaging portions 21', 21a' to 21c', the sutures 22', 22a' to 22c' in which their ends are connected the engaging portions 21', 21a' to 21c'.

The puncture needle 30' houses a plurality of, for example, in the present embodiment, four engaging portions 21', 21a' to 21c' side by side in the tip base direction.

The extrusion apparatus 40' comprised in the repeated type organ fixing instrument 100' of the present embodiment extrudes a plurality of (for example, two) engaging portions 21', 21a' one by one from the puncture needle 30' by the operation of the operation unit main body 63'.

As shown in FIG. 22, the string passages 23a' to 23d' for inserting the sutures 22', 22a', 22b' of the suturing tools 20', 20a', 20b' housed in the tip end side in the puncture needle 30' are formed at the engaging portions 21a' to 21c' of the other suturing tools 20a' to 20c' housed in the base end side.

In this specification, the side of the needle tip 31' of the puncture needle 30' is referred to as the tip end side, and the side of the puncture needle 30' that is fixed to the extrusion apparatus 40' is referred to as the base end side. In addition, the direction from the base end side to the tip end side may be referred to as the extrusion direction.

Then, the suturing tools 20', 20a' to 20c' of the present embodiment will be described in detail.

As shown in FIG. 22, a plurality of, for example, four suturing tools 20', 20a' to 20c' are loaded in the organ fixing instrument 100', and are used as a repeated type.

The suturing tools 20', 20a' to 20c' comprise the first stage of the suturing tool 20', the second stage of the suturing tool 20a', the third stage of the suturing tool 20b', and the fourth stage of the suturing tool 20c', in order from the side of the needle point 31' of the puncture needle 30', that is to say, in order from the tip end side of the puncture needle 30'. Hereinafter, the number of stages of the suturing tool means the order in which it was viewed from the tip end side of the puncture needle 30.

Next, the engaging portions 21', 21a' to 21c' are rod-shaped metal such as stainless steel, for example, cylindrical.

As shown in FIG. 21, the string passages 23a' to 23d' are formed at the engaging portions 21', 21a' to 21c', that is to say, around the engaging portion 21c' of the fourth stage of the suturing tool 20c'.

Next, as shown in FIG. 21, the string passages 23a' to 23d' of the present embodiment are formed at the peripheral surface of the engaging portion 21c' in a groove shape, along the extrusion direction of the engaging portion 21c'.

That is to say, the string passages 23a' to 23d' are formed by cutting in a semi-circular groove of the cross section recessed from the peripheral surface of the engaging portion 21c' toward the axis of the engaging portion 21c'.

In addition, although the engaging portion 21c' located at the fourth stage in FIG. 22 has been described as an example, the same structure is also provided at the engaging portions 21', 21a', 21b', located at from the other first stage to the third stage, respectively.

The width of the string passages 23a' to 23d' of the present embodiment shown in FIG. 21 is the diameter of the sutures 22', 22a' to 22c' or more. The width of the string passages 23a' to 23d' is the dimension of the string passages 23a' to 23d' as viewed in the circumferential direction of the housing portion 32' of the puncture needle 30'. Likewise, the depth of the string passages 23a' to 23d' can be the diameter of the sutures 22', 22a' to 22c' or more. The depth of the string passages 23a' to 23d' is the dimension of the string passages 23a' to 23d' as viewed in the radial direction of the housing portion 32' of the puncture needle 30'.

When the depth of the string passages 23a' to 23d' is the diameter of the sutures 22', 22a' to 22c' or more, it is possible to eliminate the protruding of the sutures 22', 22a' to 22c' from the surrounding area of the engaging portion 21c' and accommodate the sutures 22', 22a' to 22c' in the string passages 23a' to 23d'. The difference (gap dimension) of the inner diameter of the housing portion 32' and the diameter of the engaging portion 21c' except the string passages 23a' to 23d' is smaller than the diameter of the two sutures 22', 22a' to 22c', and preferably smaller than the diameter of the one suture 22', 22a' to 22c'. For this reason, when the engaging portions 21', 21a' to 21c' are pushed out in order, the sutures 22', 22a' to 22c' are not shed from the string passages 23a' to 23d', and there is no entanglement from each other.

On the other hand, when the depth of the string passages 23a' to 23d' is less than the diameter of the sutures 22', 22a' to 22c', that is to say, shallower, a part of the sutures 22', 22a' to 22c' protrudes from the circumference of the engaging portion 21c'. Therefore, although it is preferable that the depth of the string passages 23a' to 23d' is deep, it contributes to reduce the diameter of the puncture needle 30' if shallower (see the modification example shown in FIG. 32). For example, when the number of the suture is four, and the four string passages 23a' to 23d' are distributed and formed at 90 degree intervals around the circumferential direction of the engaging portion 21', the depth of each string passage (23a' to 23d') can be set to ½ of the diameter of the sutures 22', 22a' to 22c'. In this case, each suture 22', 22a' to 22c' protrudes only ½ of the diameter (radius) from the string passages 23a' to 23d'. It is possible to suppress the diameter of the circumscribed circle encompassing all of the sutures 22', 22a' to 22c' to a small diameter combining the diameter of the one suture 22', 22a' to 22c' in addition to the diameter of the engaging portion 21c'. Therefore, minimally invasive organ fixing instrument 100' is realized by reducing the diameter of the puncture needle 30'.

Figure 32:
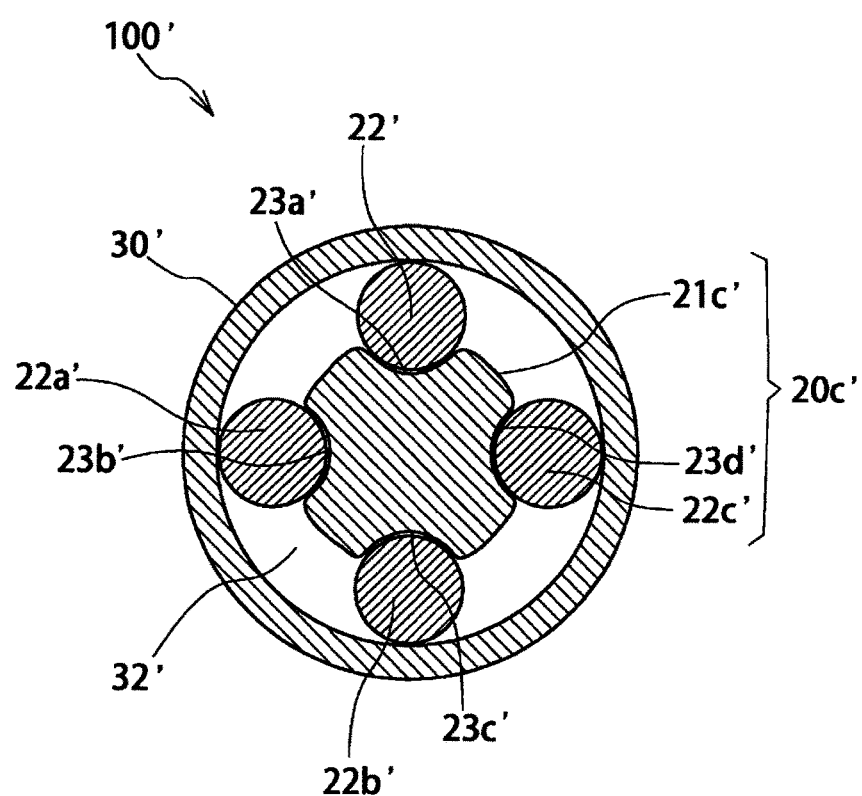
FIG. 32 A sectional view showing a modification of the organ fixing instrument of the first embodiment of the second aspect.

FIG. 32 is a sectional view showing a modification of the puncture needle 30'. The width and depth of the string passages 23a' to 23d' may be less than the diameter of the sutures 22', 22a' to 22c'. In this modification, only a part of the inner diameter side of the sutures 22', 22a' to 22c' is housed in the string passages 23a' to 23d', and the outer diameter side of the sutures 22', 22a' to 22c' is located at outside of the engaging portion 21c'. Concave string passages 23a' to 23d' is a circular arc shape along the outer peripheral surface of the sutures 22', 22a' to 22c'.

The difference of the inner diameter of the housing portion 32' and the diameter of the engaging portion 21c' which passes through the deepest portions of the facing string passages 23a' and 23c' is slightly larger than the sum of the diameter of the sutures 22' and 22b'. In addition, the difference of the inner diameter of the housing portion 32' and the diameter of the engaging portion 21c' except the string passages 23a' to 23d' is less than the sum of the diameter of the sutures 22' and 22b'.

Similarly, the difference of the inner diameter of the housing portion 32' and the diameter of the engaging portion 21c' which passes through the deepest portions of the facing string passages 23b' and 23d' is slightly larger than the sum of the diameter of the sutures 22a' and 22c'. In addition, the difference of the inner diameter of the housing portion 32' and the diameter of the engaging portion 21c' except the string passages 23a' to 23d' is less than the sum of the diameter of the sutures 22a' and 22c'.

It is the same with regard to the engaging portions 21', 21a', 21b'.

For this reason, also with regard to the organ fixing instrument 100' of this modification, when the engaging portions 21', 21a' to 21c' are pushed out in order, engaged state of the sutures 22', 22a' to 22c' are not shed from the string passages 23a' to 23d', and there is no entanglement from each other.

Next, as shown in FIG. 21, a plurality of, for example, four string passages 23a' to 23d' of the present embodiment are formed. The four string passages 23a' to 23d' are dispersed and formed at the puncture needle 30' so as to be separated from each other. The four string passages 23a' to 23d' of the present embodiment are distributed at equal intervals around the engaging portion 21' (engaging portion 21c').

Here, although the engaging portion 21c' (see FIG. 22) located at the fourth stage has been described as an example, the same structure is also provided at the engaging portions 21', 21a', 21b', located at from the other first stage to the third stage, respectively.

Although not shown, with regard to the engaging portion 21' of the first stage in the order from the side of the needle tip 31' of the puncture needle 30', one string passage through which its suture 22' passes is sufficient. However, it is also possible to provide two or more string passages.

Although not shown, with regard to the second stage of the engaging portion 21a', a total of two string passages in addition to one string passage through which its suture 22a' passes, and the first stage of the suture 22' passes, are sufficient. However, it is also possible to provide three or more string passages.

Although not shown, with regard to the third stage of the engaging portion 21b', a total of three string passages in addition to one string passage through which its suture 22b' passes, and the first stage and the second stage of the sutures 22', 22a' pass, are sufficient. However, it is also possible to provide four or more string passages.

As shown in FIG. 21, with regard to the fourth stage of the engaging portion 21c', a total of four string passages 23a' to 23d' in addition to one string passage through which its suture 22c' passes, and the first stage to the third stage of the sutures 22', 22a', 22b' pass, are sufficient. However, it is also possible to provide five or more string passages.

Then, three or more, for example, four string passages 23a' to 23d' of the present embodiment are formed. Four string passages 23a' to 23d' are evenly distributed and formed in the puncture needle 30'. That is to say, four string passages 23a' to 23d' are formed at 90 degree intervals.

In addition, although the engaging portion 21c' located at the fourth stage has been described as an example in FIG. 22, the same structure is also provided at the engaging portions 21', 21a', 21b', located at from the other first stage to the third stage, respectively.

In organ fixing instrument 100' of the present embodiment, the same number (4 pieces) of string passages 23a' to 23d' as the number of all of the sutures 22', 22a' to 22c' are formed at the engaging portions 21', 21a' to 21c', respectively. Thus, with regard to the engaging portions 21', 21a' to 21c', it is possible to be the same shape each other. Accordingly, it contributes to the reduction in the number of components.

The sutures 22', 22a' to 22c' of the present embodiment are made of resin such as nylon. The sutures 22', 22a' to 22c' are provided one by one at the engaging portions 21', 21a' to 21c'. One end of each of the sutures 22', 22a' to 22c' is heat-sealed or adhesively fixed to the middle of the length of the engaging portions 21', 21a' to 21c', for example, the central portion or the like of the engaging portions 21', 21a' to 21c' or fixed around the engaging portions 21', 21a' to 21c' by swaging. The other end of the sutures 22', 22a' to 22c' is derived to the outside of the organ fixing instrument 100'.

The puncture needle 30' is a needle made of metal cylinder such as stainless steel. As shown in FIG. 22, the engaging portions 21', 21a' to 21c' are housed in the housing portion 32' in the puncture needle 30' into which the engaging portions are freely inserted. The housing portion 32' is hollow, and its whole length is set to the length of four pieces of the engaging portions 21', 21a' to 21c' or more. That is to say, the housing portion 32' can house a plurality of, for example, four engaging portions 21', 21a' to 21c' along the axial direction of the puncture needle 30'.

The housing portion 32' has one end portion open to the needle tip 31' and the other end portion which communicates with the extrusion apparatus 40'. As shown in FIG. 21, the diameter of the housing portion 32', namely the inner diameter of the puncture needle 30' is slightly larger than the diameter of the engaging portions 21', 21a' to 21c'.

Then, the extrusion apparatus 40' of the present embodiment will be described in detail.

The extrusion apparatus 40' is for performing the repeating type operation. For convenience, the extrusion apparatus capable of loading and sending the two suturing tools 20', 20a' in order will be described as an example.

With regard to the extrusion apparatus 40', as shown in FIGS. 23 to 28, when roughly divided, it comprises a cylindrical portion 50', an operation unit 60', a grip portion 70', and a locking device 80'.

The cylindrical portion 50' is a cylinder made of synthetic resin, as shown in FIGS. 23 to 25, the puncture needle 30' is fixed to the cylinder. The cylindrical portion 50' is open at both ends, the base end portion which is the opposite side of the needle tip 31' of the puncture needle 30' is fixed to one opening end portion, the inside of the cylindrical portion 50' communicates with the housing portion 32' of the puncture needle 30' through this one end portion, and the operation unit 60' is inserted into the opening of the other end portion. As shown in FIG. 25, the thread exit hole 51' penetrating the inside and outside is provided at the cylindrical portion 50'. Although not shown, the two sutures 22', 22a' derived to the inside of the cylindrical portion 50' through the housing portion 32' of the puncture needle 30' via the string passages 23a' to 23d' of the engaging portions 21', 21a' pass through the thread exit hole 51'.

The operation unit 60' extrudes the engaging portions 21', 21a' housed in the housing portion 32' of the puncture needle 30' from the needle tip 31' of the puncture needle 30' through the interior of the cylindrical portion 50'. The operation unit 60' comprises a push rod 61', a pressing portion 62', and an operation unit main body 63', as shown in FIGS. 23 to 28, when roughly divided.

The push rod 61' is a metal mandrel such as stainless steel. As shown in FIGS. 25 and 29, the push rod 61' extrudes the engaging portions 21', 21a' housed in the housing portion 32' from the needle tip 31' by being inserted into the housing portion 32' of the puncture needle 30' from the interior of the cylindrical portion 50', and sliding in the housing portion 32'. That is to say, since the first stage of the engaging portion 21' and the second stage of the engaging portion 21a' positioned at the next stage are accommodated in the housing portion 32' in this order from the needle tip 31', the push rod 61' comes into contact with the second stage of the locking portion 21a'. When the push rod 61' proceeds to the needle tip 31' side (tip end side of the puncture needle 30'), the second stage of the engaging portion 21a' proceeds to the needle tip 31' side by being pushed by the push rod 61'. Therefore, the first stage of the engaging portions 21' proceeds to the needle tip 31' side by being pushed by the second stage of the engaging portion 21a'.

The pressing portion 62' is a cylinder made of synthetic resin. As shown in FIG. 25, the push rod 61' is fixed to one end of the pressing portion 62'. The other end of the pressing portion 62' reaches the operation unit main body 63' described later, and it is intended to transmit the pressure of the operation unit main body 63' to the push rod 61'. The pressing portion 62' is slidably held in the cylindrical portion 50', and projects from the opening of the other end at the upper side to the outside of the cylindrical portion 50' which opens upward in the same figure.

The operation unit main body 63' is a disk-shaped synthetic resin, as shown in FIGS. 25 to 28, it is intended to perform the pressing operation. As shown in FIG. 23, the operation unit main body 63' protrudes into a disc shape from the upper end of the pressing portion 62' located at the upper side in the same figure. The outer diameter of the operation unit main body 63' is set to larger than the inner diameter of the opening of the other end of the cylindrical portion 50' which opens upward in the same figure in order not to be accidentally buried in the cylindrical portion 50'.

The gripping portion 70' is a flat plate-shaped synthetic resin and it is intended to grip the extrusion apparatus 40'. As shown in FIG. 23, the gripping portion 70' symmetrically protrudes toward the both of the left and right sides in plates from the lower side of the cylindrical portion 50' in the same figure.

The locking device 80' is a device which regulates the operation unit 60' so as not to inadvertently slide against the cylindrical portion 50'. As shown in FIG. 25, the locking device 80' comprises the engaging claw 81', the recessed portions 82', 82a', when roughly divided. In addition to this, the cylindrical portion 50' is provided with the release buttons 83' and 84' for releasing the locked state of the locking device 80'.

The pressing of the operation unit 60' to the cylindrical portion 50' is prevented by fitting of the engaging claw 81' into one of the recessed portions 82', 82a'.

As shown in FIGS. 25 to 27, the engaging claw 81' is provided at the pressing portion 62' and protrudes from the outer periphery in convex form. The pressing portion 62' is formed in a cylindrical shape, and the outer peripheral wall is cut. Thus, the convex portion is possible to elastically deflect to the inside of the cylinder.

As shown in FIG. 25, the recessed portions 82', 82a' are provided at the cylindrical portion 50', and are provided at upper and lower two stages in the same figure.

The recessed portions 82', 82a' penetrate inside and outside of the cylindrical portion 50', the engaging claw 81' fits from the inner peripheral side of the cylindrical portion 50', and the release buttons 83' and 84' described later are attached on the outer side, respectively.

In a state in which the engaging claw 81' is fitted into the recessed portion 82' located at the upper side of FIG. 24, as shown in FIG. 28, the tip of the push rod 61' faces the second stage housed within the housing portion 32' of the puncture needle 30', that is to say, the engaging portion 21a' which is located at the upper side in the same figure.

In a state in which the engaging claw 81' is fitted into the recessed portion 82' located at the upper side, the operation unit 60' is prevented from further being pushed into the interior of the cylindrical portion 50', the suturing tools 20', 20a' are prevented from being extruded from the needle tip 31' of the puncture needle 30'. The operation unit 60' is also prevented from coming out from the inside of the cylindrical portion 50'.

When the engaging claw 81' which has been fitted into the recessed portion 82' located at the upper side, proceeds toward the recessed portion 82a' located at the lower side in FIG. 24, the second stage of engaging portion 21a' proceeds to the needle tip 31' side by being pushed by the push rod 61'. Therefore, the first stage of the engaging portion 21' is pushed out from the needle tip 31' by being pushed by the second stage of the engaging portion 21a'.

In this position, the engaging claw 81' is fitted into the recessed portion 82a' located at the lower side. In a state in which the engaging claw 81' is fitted into the recessed portion 82a' located at the lower side, the operation unit 60' is prevented from further being pushed into the interior of the cylindrical portion 50', and the second stage of the suturing tool 20a' is prevented from being extruded from the needle tip 31' of the puncture needle 30'.

The release buttons 83' and 84' are button type comprising synthetic resin. As shown in FIG. 25, they push the engaging claw 81' that fits into one of the recessed portions 82', 82a' in the direction from the recessed portions 82', 82a' to the inside of the cylindrical portion 50', namely, radially inward toward the center of the cylindrical portion 50'.

As a result, the engaging claw 81' is disengaged from the recessed portions 82', 82a', and the locking state is released.

As shown in FIG. 25, the release buttons 83' and 84' fit into the upper and lower recessed portions 82', 82a' from the outer periphery of the cylindrical portion 50', although not shown, and project from the outer circumference by the spring force of the leaf spring or coil spring.

The method of using the organ fixing instrument 100' of the present embodiment will be described.

The organ fixing instrument 100' is used in a state in which the engaging claw 81' is fitted into the recessed portion 82' located at the upper side in FIG. 25.

As shown in FIG. 29, the puncture needle 30' is punctured from the outside of the patient's body until penetrating the body wall (abdominal wall) A' and stomach wall B', thereby exposing the needle tip 31' within the gastric cavity.

Next, as shown in FIG. 30, the release button 83' located at the upper side in the same figure is pressed. When pressing the release button 83', the engaging claw 81' which is fitted into the recessed portion 82' located at the upper side in the same figure is disengaged, and the locked state of the locking device 80' is released.

Then, as shown in FIG. 30, the operation unit main body 63' is pressed toward the inside of the cylindrical portion 50'.

When pressing the operation unit main body 63', the push rod 61' is advanced through the housing portion 32' of the puncture needle 30', via the second stage of the engaging portion 21a', and the first stage of the engaging portion 21' is pushed out from the needle tip 31'.

Therefore, as shown in FIG. 30, the first stage of the engaging portion 21' is introduced into the stomach.

The organ fixing instrument 100' is recovered by pulling out the puncture needle 30' to the outside of the body.

Then, as shown in FIG. 31, by pulling the suture 22' of the first stage of the engaging portion 21' from the outside of the body, the engaging portion 21' attracts the stomach wall B' to the body wall A'. Then, the stomach wall B' is fixed to the body wall A' by fixing the suture 22' to the outside of the body.

Then, although not shown, the puncture needle 30' of the recovered organ fixing instrument 100' is punctured from different position of the body wall A' until penetrating stomach wall B', thereby exposing the needle tip 31' within the stomach.

Then, the release button 84' located at the lower side in FIG. 25 is pressed. When pressing the release button 84', the engaging claw 81' fitted into the recessed portion 82a' positioned at the lower side in the same figure, is disengaged, and the locked state of the locking device 80' is released.

Then, the operation unit main body 63' is pressed toward the inside of the cylindrical portion 50'.

When pressing the operation unit main body 63', the push rod 61' is advanced through the housing portion 32' of the puncture needle 30', and the second stage of the engaging portion 21a' is pushed out from the needle tip 31'. Therefore, the second stage of the engaging portion 21a' is introduced into the stomach.

Similarly to the first stage of the suture 22', by pulling the suture 22a' of the second stage of the engaging portion 21a' from outside the body and fixing, the stomach wall B' is fixed to the body wall A'.

As stated above, the extrusion apparatus 40' for loading and feeding two suturing tools 20', 20a' in order is explained. However, the present invention is not limited thereto. As shown in FIGS. 21 and 22, in the case of four-repeated organ fixing instrument 100', in which the four engaging portions 21', 21a' to 21c' are loaded in the puncture needle 30' and are fed in order, further two release buttons can be provided at the extrusion apparatus 40' in addition to the release buttons 83', 84'. Thus, it is possible to set the quantity of the recessed portion 82' and the release button 83' provided at the extrusion apparatus 40' according to the number of the engaging portions to be loaded.

Second Embodiment

Figure 33:
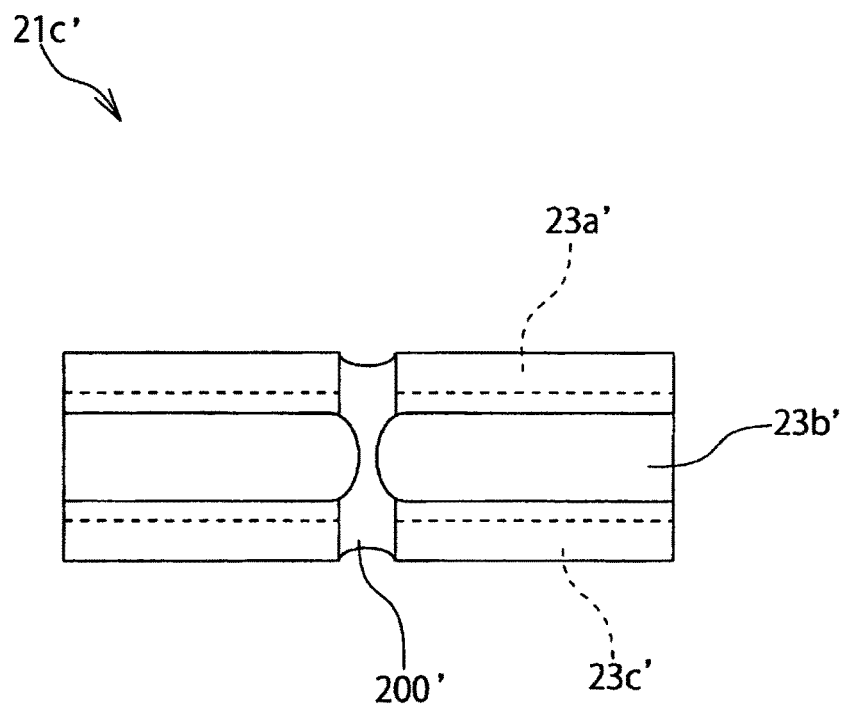
FIG. 33 A plan view showing the engaging portion of the second embodiment of the second aspect of the present invention.
Figure 34:
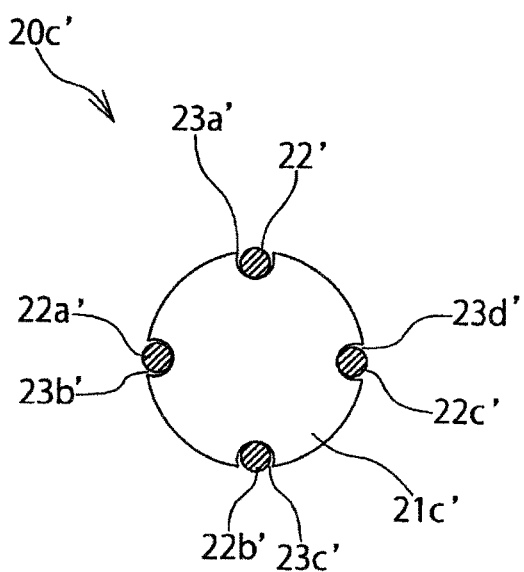
FIG. 34 A sectional view showing the suturing tool of the second embodiment of the second aspect.

FIG. 33 is a plan view showing the engaging portion of the second embodiment of the second aspect of the present invention. FIG. 34 is a sectional view showing the suturing tool.

The suturing tool 20c' of the present embodiment differs from the first embodiment in that the fixing groove 200' is formed at the locking portion 21c'.

The annular fixing groove 200' for fixing by tying the suture 22c' is formed around the middle portion in the length direction (longitudinal direction) of the engaging portion 21c' of the present embodiment. The fixing groove 200' of the present embodiment is formed at the center of the length direction (longitudinal direction) of the engaging portion 21c' in a ring extending in a direction perpendicular to the string passages 23a' to 23d'.

As shown in FIG. 33, the fixing groove 200' is made by cutting from the circumferential surface of the engaging portion 21c' toward the axis of the engaging portion 21c' in a recessed, semi-circular groove in a cross-section.

In addition, although the engaging portion 21c' located at the fourth stage has been described as an example in FIG. 22, the same structure is also provided at the engaging portions 21', 21a', 21b', located at from the other first stage to the third stage, respectively.

The inner diameter of the fixing groove 200' is the diameter of the suture 22c' or more. The depth of the fixing groove 200' is formed less than the diameter of the suture 22c', and formed shallower compared with the string passages 23a' to 23d'.

With regard to the relationship of the depth of the fixing groove 200' and the diameter of the suture 22c', it is possible to eliminate the protrusion of the suture 22c' from the circumference of the engaging portion 21c' if the depth of the fixing groove 200' is set to the diameter of the suture 22c' or more as well as the depth of the string passages 23a' to 23d'.

On the other hand, if the depth of the fixing groove 200' is set to less than the diameter of the suture 22c', that is to say, set to be shallow, a part of the diameter dimension of the suture 22c' protrudes from the circumference of the engaging portion 21c'. In terms of diameter reduction of the puncture needle 30', the depth of the fixing groove 200' can be deepened.

The method of fixing the suture 22c', as well as the method of mounting the puncture needle (not shown) will be described with reference to FIGS. 33 and 34.

One end of the suture 22c' is wound around the fixing groove 200' and the tip portion is fixed to the middle of the length of the wound suture by tying. Then, the engaging portion 21' is inserted into the puncture needle 30 (see FIG. 22). At this time, as shown in FIG. 34, the suture 22c' may be inserted into the interior of the puncture needle 30' in a state in which the suture is allowed along the string passage 23d'.

Third Embodiment

Figure 35:
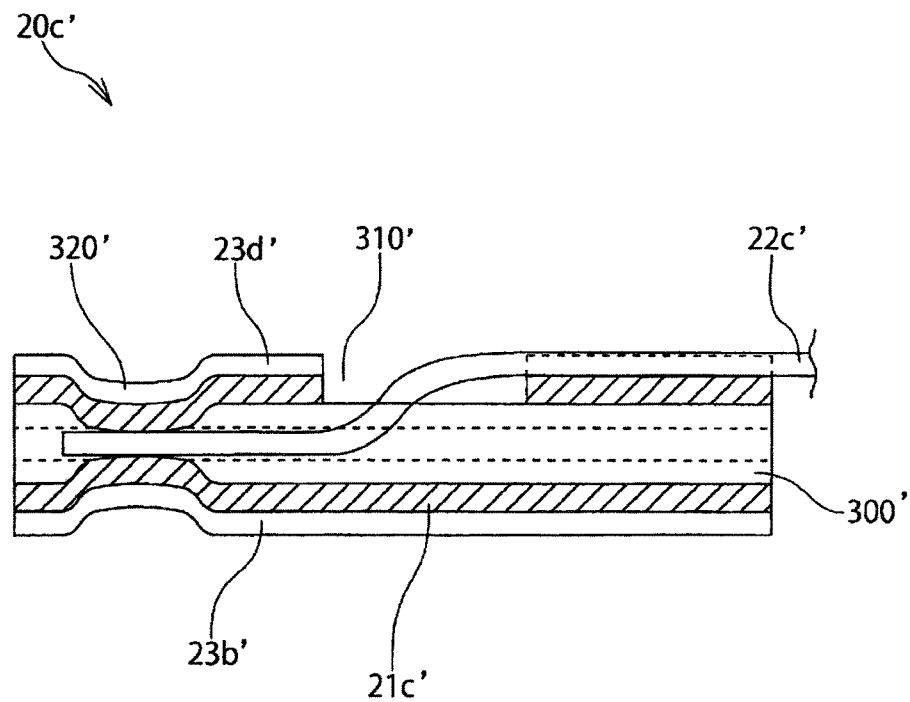
FIG. 35 A partial sectional view showing the suturing tool of the third embodiment of the second aspect of the present invention.
Figure 36:
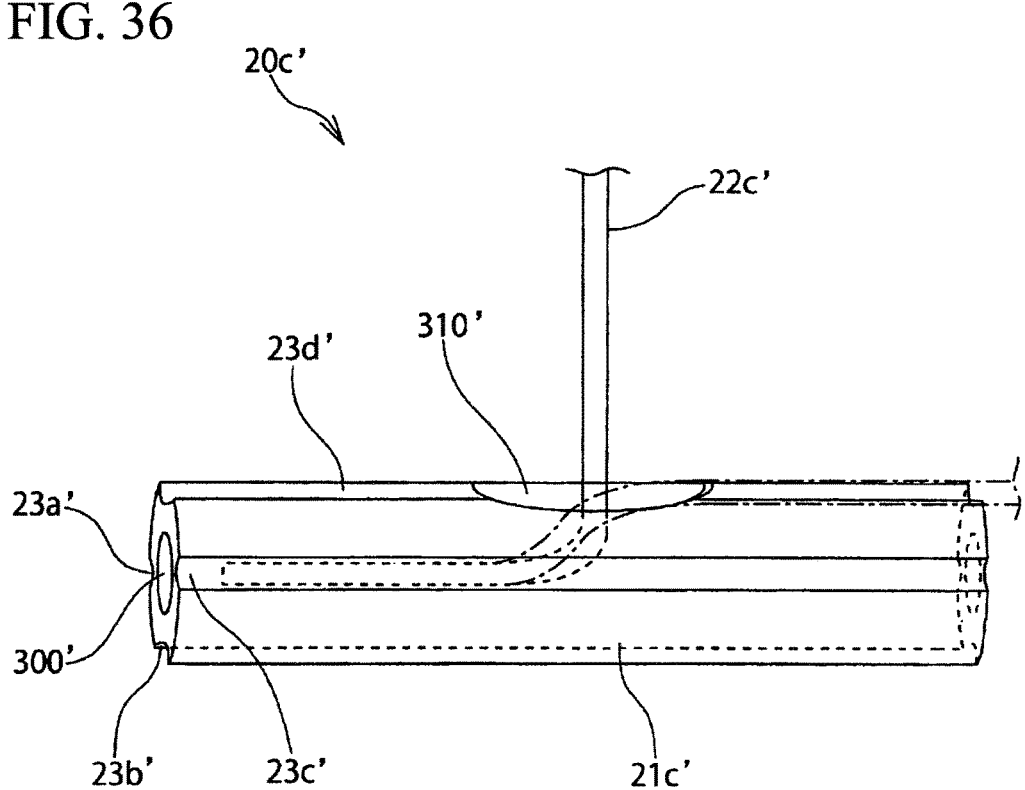
FIG. 36 A partial perspective view showing the suturing tool of the third embodiment of the second aspect.
Figure 37:
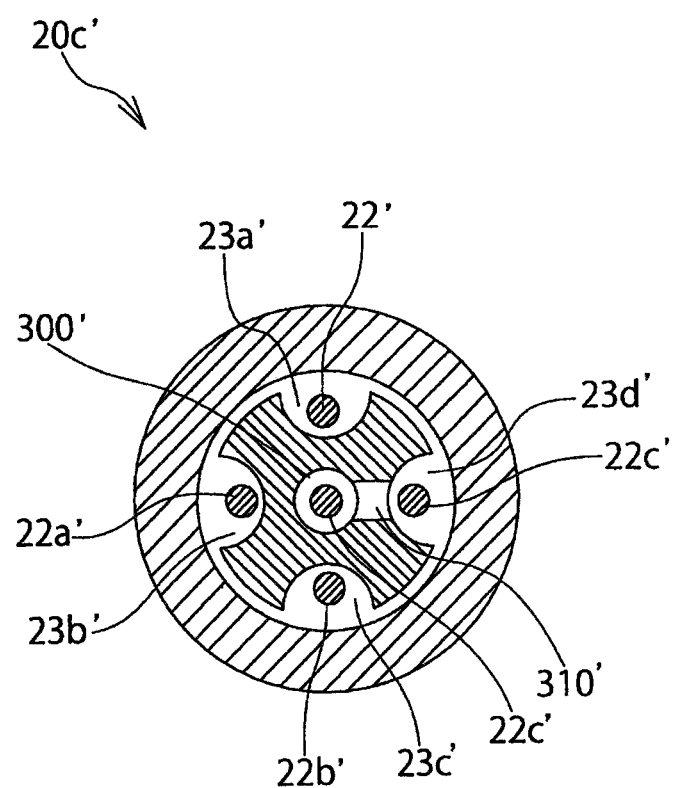
FIG. 37 A sectional view showing the suturing tool of the third embodiment of the second aspect.

FIG. 35 is a partial sectional view showing the suturing tool 20c' of the third embodiment of the second aspect of the present invention. FIG. 36 is a partial perspective view showing the suturing tool 20c'. FIG. 37 is a sectional view showing the suturing tool 20c'.

The suturing tool 20c' of the present embodiment differs from the first embodiment in that the engaging portion 21c' has a hollow structure, and the suture 22c' is fixed within the hollow portion 300'.

The engaging portion 21c' of the present embodiment is formed to be hollow. The through hole 310' penetrating inside and outside of the engaging portion 21c' is formed at the middle of the length. The suture 22c' inserted from the through hole 310' is fixed to the inside of the hollow by swaging around the engaging portion 21c'. The suture 22c' derived from the through hole 310' to the outside is inserted into any of the string passages 23a' to 23d'.

In addition, although the engaging portion 21c' located at the fourth stage has been described as an example in FIG. 22, the same structure is also provided at the engaging portions 21', 21a', 21b', located at from the other first stage to the third stage, respectively.

The engaging portion 21c' of the present embodiment is made of a metal such as stainless steel and formed into a hollow cylindrical shape. The diameter of the hollow portion 300' of the engaging portion 21c' is set to the diameter of the suture 22c' or more. The through hole 310' penetrates the hollow portion 300' from the string passage 23d' side, and the opening shape is elliptically formed. The inner diameter of the through hole 310' is set to the diameter of the suture 22c' or more. The opening shape of the through hole 310' of the present embodiment may be linear (slit), oval, square or polygonal shape in addition to the elliptical shape.

The method for fixing the suture 22c' and the method for mounting to the puncture needle 30' will be described with reference to FIGS. 35 to 37.

As shown in FIG. 36, one end of the suture 22c' is inserted into the hollow portion 300' through the through hole 310' from the outside of the engaging portion 21c'.

Next, as shown in FIG. 35, the periphery of the engaging portion 21c' through which the suture 22c' passes is swaged, thereby forming the swaged portion 320'. The engaging portion 21c' is narrowed by the swaging portion 320', and the inner wall bites the suture 22c'. In this manner, the suture 22c' is fixed in the hollow portion 300', and the suture 22c' is prevented from falling off from the through hole 310'.

Then, the engaging portion 21c' is inserted into the housing portion 32' of the puncture needle 30'. In this case, as shown in FIG. 37, the swaged portion 320' is inserted toward the needle tip side of the puncture needle 30', and the suture 22c' coming out from the through hole 310' is derived to the outside of the puncture needle 30' along the string passage 23d'.

Here, although the engaging portion 21c' located at the fourth stage has been described as an example in FIG. 22, the same is true on the engaging portions 21', 21a', 21b', located at from the remaining first stage to the third stage, respectively. Although not shown, the through hole of the first stage of the engaging portion 21' is formed in the middle of the string passage 23a'. The suture 22' is inserted into the inside of the puncture needle 30' along the string passage 23a'.

The through hole of the second stage of the engaging portion 21a' is formed in the middle of the string passage 23b'. The suture 22a' is inserted into the inside of the puncture needle 30' along the string passage 23b'. The through hole of the third stage of the engaging portion 21b' is formed in the middle of the string passage 23c'. The suture 22b' is inserted into the inside of the puncture needle 30' along the string passage 23c'. Thus, four engaging portions 21', 21a' to 21c' can be the same shape with each other.

Fourth Embodiment

Figure 38:
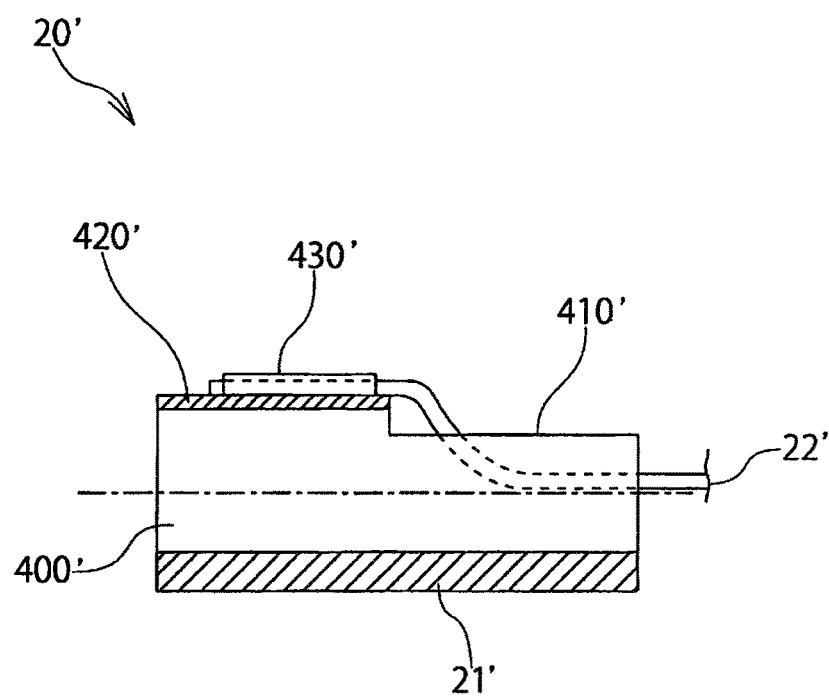
FIG. 38 A partial sectional view showing the suturing tool of the fourth embodiment of the second aspect of the present invention.
Figure 39:
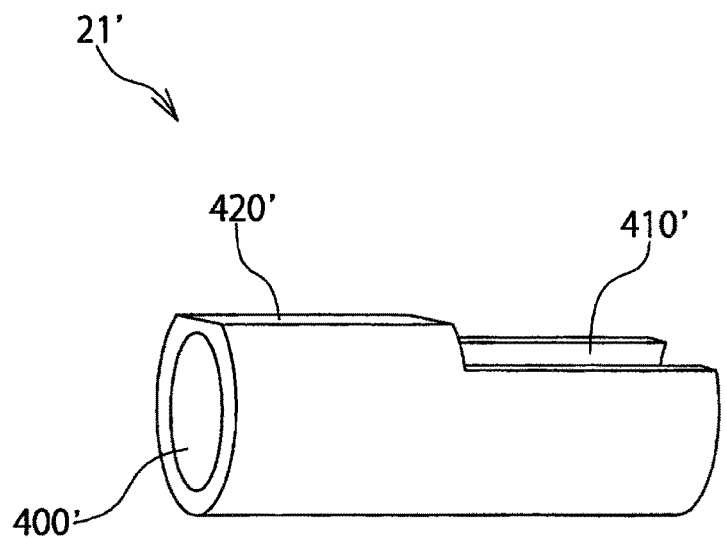
FIG. 39 A perspective view showing the engaging portion of the fourth embodiment of the second aspect.

FIG. 38 is a partial sectional view showing the suturing tool 20' of the fourth embodiment of the second aspect of the present invention. FIG. 39 is a perspective view showing the engaging portion.

First, the suturing tool 20' of the present embodiment differs from the first to third embodiments in that the first engaging portion 21' has the hollow structure, and the hollow portion 400' is used as a "string passage".

Second, the suturing tool 20' of the present embodiment differs from the first to third embodiments in that the flat portion 420' is formed around the engaging portion 21', and the first suture 22' is bonded to the flat portion 420'.

Hollow is formed in the engaging portion 21' of the present embodiment. The present embodiment is characterized in that the internal hollow cylinder of the engaging portion 21', that is to say, the hollow portion 400' is the string passage.

In addition, the flat portion 420' which can bond the suture 22' is formed at the circumference of the engaging portion 21'. Furthermore, not only the engaging portion 21' located at the first stage, but also the engaging portions 21a' to 21c' respectively located at the second stage to the fourth stage have the same structure.

The slit 410' extending from the surface of the base end side to the middle of the length, that is to say, extending from the surface of the base end side to the base end side of the surface of the tip end side, is formed at the engaging portion 21'. The suture 22' is bonded to either side of the inner and outer peripheral surface of the tip end side of the engaging portion 21', for example, the flat portion 420' located at the outside. Bonded suture 22' is retracted to the inside of the hollow cylinder of the engaging portion 21', that is to say, the inside of the hollow portion 400', via the slit 410'. In addition, although the engaging portion 21' located at the first stage has been described as an example in FIG. 22, the same structure is also provided at the engaging portions 21a' to 21c', located at from the other second stage to the fourth stage, respectively.

The engaging portion 21' of the present embodiment is made of metal such as stainless steel, and is formed into a hollow cylindrical shape. The slit 410' and the flat portion 420' are adjacently positioned, and are formed respectively at the divided halves of the engaging portion 21'. The slit 410' is positioned at the base end side of the engaging portion 21' when it is inserted into the puncture needle 30', and the flat portion 420' is positioned at the needle tip side of the puncture needle.

The groove width of the slit 410' is set to the diameter of the suture 22' or more. The width of the flat portion 420' is set to the diameter of the suture 22' or more.

The method for fixing the suture 22', and the method for mounting to the puncture needle 30' (see FIG. 22) will be described with reference to FIG. 38.

As shown in FIG. 38, one end of the suture 22' is positioned at the flat portion 420' of the engaging portion 21', heat sealing or bonded fixing, or fixing by swaging around the flat portion 420', thereby forming the fixed portion 430'. In FIG. 38, the case of heat sealing or bonded fixing is illustrated. In this case, the tip portion of the suture 22' is positioned at the opposite side of the slit 410', that is to say, toward the needle tip side when it is inserted into the puncture needle.

Then, the engaging portion 21' is inserted into the puncture needle 30'. In this case, although not shown, the fixing portion 430' is inserted toward the needle tip side of the puncture needle. As shown in FIG. 38, the suture 22' is derived to the outside through the hollow portion 400' which is the "string passage" after being derived to the inside of the hollow portion 400' through the slit 410'.

Fifth Embodiment

Figure 40:
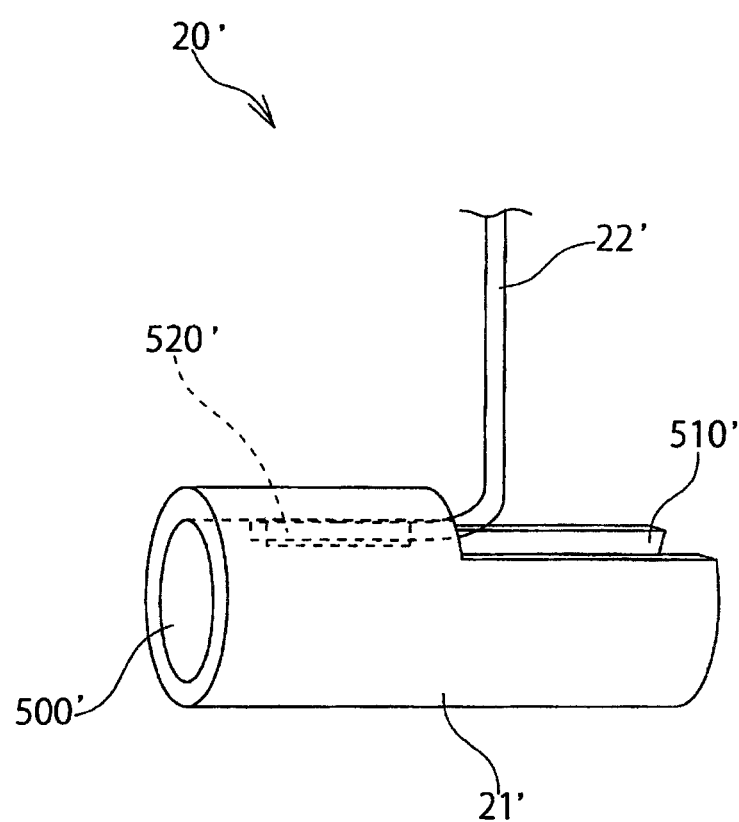
FIG. 40 A partial perspective view showing the suturing tool of the fifth embodiment of the second aspect of the present invention.

FIG. 40 is a partial perspective view showing the suturing tool 20' of the fifth embodiment of the second aspect of the present invention.

The suturing tool 20' of the present embodiment differs from the first to the fourth embodiments in that the engaging portion 21' has the hollow structure, and the suture 22' is bonded to the inner peripheral surface of the hollow portion 500'.

The suture 22' is bonded to the inside of the tip end side of the cylinder of the engaging portion 21' of the present embodiment.

In addition, although the engaging portion 21' located at the first stage has been described as an example in FIG. 22, the same structure is also provided at the engaging portions 21a' to 21c', located at from the other second stage to the fourth stage, respectively.

The engaging portion 21' of the present embodiment is made of a metal such as stainless steel and is formed into a hollow cylindrical shape. The hollow interior of the cylinder of the engaging portion 21', that is to say, the hollow portion 500' is used as the string passage.

The slit 510' extending to the middle of the length from the end face of the base end side is formed at the engaging portion 21'. The slit 510' is formed at one halve of the engaging portion 21'. The slit 510' is positioned at the base end side when the engaging portion 21' is inserted into the puncture needle 30' (see FIG. 22). The groove width of the slit 510' is set to the diameter of the suture 22' or more.

The method for fixing the suture 22' to the engaging portion 21', and the method for mounting to the puncture needle (not shown) will be described with reference to FIG. 40.

As shown in FIG. 40, one end of the suture 22' is inserted into the hollow portion 500' through the slit 510'. Then, the tip of the one end of the suture 22' is positioned at the inner wall surface of the hollow portion 500' and forming the fixed portion 520' by heat sealing or bonded fixing. In this case, the tip portion of the suture 22' is positioned at the opposite side of the slit 510', that is to say, toward the needle tip side when it is inserted into the puncture needle.

Then, the engaging portion 21' is inserted into the puncture needle 30'. In this case, the fixing portion 520' is inserted toward the needle tip side of the puncture needle 30'. As shown in FIG. 40, the suture 22' is derived to the outside of the puncture needle 30' through the hollow portion 500' which is the "string passage" after being derived into the inside of the hollow portion 500' through the slit 510'.

Sixth Embodiment

Figure 41:
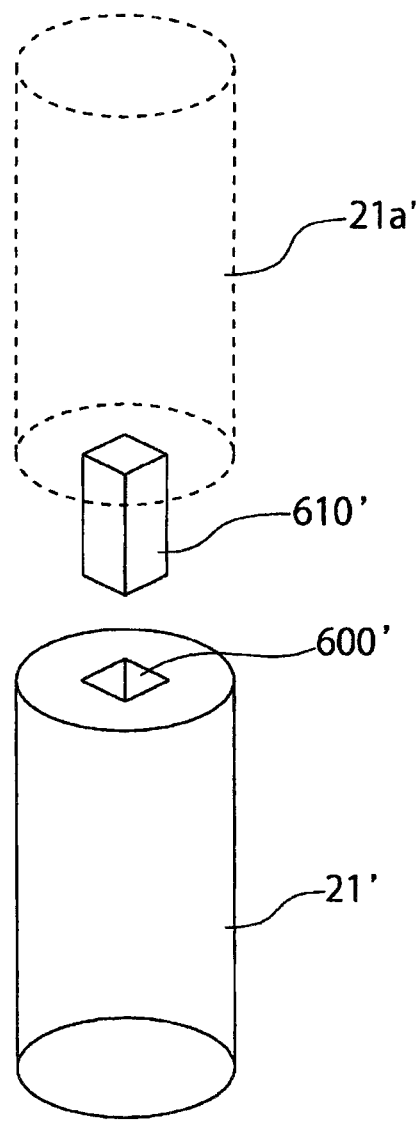
FIG. 41 A partial perspective view showing the engaging portion of the sixth embodiment of the second aspect of the present invention.

FIG. 41 is a partial perspective view of the engaging portion of the sixth embodiment of the second aspect of the present invention.

The present embodiment differs from the first to the fifth embodiments in that the uneven portions 600', 610' fitted into each other are formed at the end surface of the engaging portions 21', 21a'.

The uneven portions 600', 610' fitted into each other are formed at the end surface of at least a pair of the facing engaging portions 21', 21a'.

In addition, although not shown and the engaging portions 21', 21a' located at the first stage and the second stage have been described as examples in FIG. 22, the similar structure of the uneven portions are provided between the engaging portion 21a' located at the second stage and the engaging portion 21b' located at the third stage, and between the engaging portion 21b' located at the third stage and the engaging portion 21c' located at the fourth stage.

The uneven portions 600', 610' are formed so that their cross-section is non-circular. Among the uneven portions 600', 610', the recessed portion 600' is formed at the end surface of the base end side of the first stage of the engaging portion 21' in FIG. 22 (upper side in FIG. 41). The horizontal section of the recessed portion 600' of the present embodiment is a concave square. The horizontal section is a cross-section cut in a direction perpendicular to the axial direction of the engaging portion 21'. The recessed portion 600' is bottomed, and extends concavely in the axial direction from the center of the end surface of the engaging portion 21'. The convex portion 610' is formed to prismatically protrude at the center of the end surface of the tip side (lower side of FIG. 41) of the engaging portion 21a'. The horizontal sectional shape of the convex portion 610' corresponds to the recessed portion 600'. The convex portion 610' of the engaging portion 21a' is fitted into the recessed portion 600' of the end surface of the base end side (upper side in FIG. 41) of the other engaging portion 21' which is located at the tip end side. With regard to the relationship of the depth of the recessed portion 600' and the total length of the convex portion 610', the depth of the recessed portion 600' may be the total length of the convex portion 610' or more.

Although not shown, two engaging portions 21', 21a' regulate the relative rotation of the adjacent engaging portions 21', 21a' around the axis when they are inserted into the puncture needle by fitting the uneven portions 600', 610' each other. Thus, for example, in the case of applying the sixth embodiment to the fifth embodiment, the sutures 22', 22a' can be prevented to be twisted and entangled each other in the hollow portion 500'.

It should be noted that the present invention is not limited to the embodiments described above, the present invention includes aspects of various modifications and improvements or the like as long as the object of the present invention is achieved.

For example, along with the engaging portion may be formed to be hollow so as to make the cylindrical inside as the string passage, other string passage may be formed at the peripheral surface of the engaging portion in a groove shape. Thus, when the number of sutures is large, it is possible to insert a portion of the sutures through the tubular interior and pass the other sutures through the groove-like string passage of the peripheral surface of the engaging portion. Therefore, it is possible to reduce the entanglement between the sutures.

In addition, a plurality of independent string passages may be formed as through holes in the engaging portion, and each suture may be inserted into each through hole one by one.

In the first embodiment, although the engaging portion has a cylindrical shape, it may have a hollow cylindrical shape instead of the cylindrical shape. In addition, the cross-sectional shape of the engaging portion is not limited to a circle, it may be polygonal.

For example, in the first embodiment, although the suturing tool in which each one suture is fixed to the engaging portion is illustrated, the present invention is not limited thereto. It is also possible to fix a plurality of sutures to the engaging portion.

In the above embodiment, although a state of fixing the suture in the center of the engaging portion has been illustrated, the suture may be fixed to the end of the engaging portion, or one of the sutures may be looped and the both ends may be respectively fixed to the both ends of the engaging portion.

As shown in FIG. 21, in the above first and second embodiments, although the horizontal sectional shape of the string passages $23a'$ to $23d'$ is semi-circular, it is not limited thereto. The horizontal sectional shape of the string passage may be, for example, U-shape, Ω-shape, rectangular or polygonal.

For example, in the first embodiment, although the four string passages $23a'$ to $23d'$ are formed and evenly distributed around the engaging portions $21'$, $21a'$ to $21c'$, the four string passages $23a'$ to $23d'$ may be formed and non-uniformly distributed around the engaging portions $21'$, $21a'$ to $21c'$.

For example, in the first embodiment, although the number of the suturing tools $20'$, $20a'$ to $20c'$ is four, it may be two, three or five or more.

In the second embodiment, although the fixing groove $200'$ is formed in the center of the engaging portion $21c'$, it may be formed at the position closer to one end.

For example, in the second embodiment, although fixing one end of the suture $22c'$ to the fixing groove $200'$ by tying is illustrated, it may be heat sealing or bonding instead of it.

The above embodiments include the following technical ideas.

(1) A repeated type organ fixing instrument having a plurality of suturing tools comprising a rod-shaped engaging portion, a suture in which an end thereof is fixed to the engaging portion, and a puncture needle for housing a plurality of the engaging portions side by side in a tip base direction, wherein a plurality of the engaging portions are extruded one by one from the puncture needle by the operation of a operation unit main body, and wherein a string passage for inserting the suture of the suturing tool housed at a tip end side into an inside of the puncture needle is formed at the engaging portion of other suturing tool housed at a base end side.

(2) The repeated type organ fixing instrument according to (1), wherein the engaging portion is formed to be hollow and an inside of a hollow cylinder of the engaging portion is the string passage.

(3) The repeated type organ fixing instrument according to (2), wherein a flat portion capable of bonding the suture is formed at a peripheral surface of the engaging portion.

(4) The repeated type organ fixing instrument according to (2) or (3), wherein a slit extending from the surface of the base end side to the base end side of the surface of the tip end side is formed at the engaging portion, wherein the suture is bonded to either side of the inner and outer peripheral surface of the tip end side of the engaging portion, and wherein the bonded suture is retracted to the inside of the hollow cylinder of the engaging portion via the slit.

(5) The repeated type organ fixing instrument according to any one of (2) to (4), wherein the suture is bonded to the inside of the cylinder of the tip end side of the engaging portion.

(6) The repeated type organ fixing instrument according to any one of (1) to (5), wherein the string passage is formed in a groove shape at the peripheral surface of the engaging portion along an extrusion direction of the engaging portion.

(7) The repeated type organ fixing instrument according to any one of (1) to (6), wherein a plurality of the string passages are formed and a plurality of the string passages are formed and dispersed so as to be separated with each other.

(8) The repeated type organ fixing instrument according to (7), wherein three or more string passages are formed and a plurality of the string passages are evenly formed and dispersed in the circumferential direction on the surface of the engaging portion.

(9) The repeated type organ fixing instrument according to any one of (1) to (8), wherein an annular fixing groove for fixing by tying the suture is formed around the middle portion in the longitudinal direction of the engaging portion.

(10) The repeated type organ fixing instrument according to any one of (1) to (9), wherein an uneven portion is formed at the end surface of the engaging portion and the uneven portion and the uneven portion of other adjacent engaging portion are fitted into each other.

(11) The repeated type organ fixing instrument according to (10), wherein the uneven portion is formed so that a cross-section is non-circular.

(12) The repeated type organ fixing instrument according to any one of (1) to (11), wherein the engaging portion is formed to be hollow, wherein an through hole penetrating inside and outside of the engaging portion is formed at the middle in the longitudinal direction, the suture inserted from the through hole is fixed to the inside of the hollow by swaging around the engaging portion, and wherein the suture derived from the through hole to the outside is inserted into the string passage.

EXPLANATION OF REFERENCE 20, 20a to 20c Suturing tool
21, 21a to 21c Engaging portion
22, 22a to 22c Suture
30 Puncture needle
31 Needle tip
32 Housing portion
33 Slit (Penetrating portion)
40 Extrusion apparatus
50 Cylindrical portion
51 Thread exit hole
60 Operation unit
61 Push rod
62 Pressing portion
63 Operation unit main body
70 Gripping portion
80 Locking device
81 Engaging claw
82, 82a Recessed portion
83, 84 Release button
100 Organ fixing instrument
200, 400 Slit 300 Traverse hole (Penetrating portion)
310 Inclined portion
500 to 503 Recessed portion
A Skin side wall
B Stomach wall
20', 20a' to 20c' Suturing tool
21', 21a' to 21c' Engaging portion
22', 22a' to 22c' Suture
23a' to 23d' String passage
30' Puncture needle
31' Needle tip
32' Housing portion
40' Extrusion apparatus
50' Cylindrical portion
51' Thread exit hole
60' Operation unit
61' Push rod
62' Pressing portion
63' Operation unit main body
70' Gripping portion
80' Locking device
81' Engaging claw
82', 82a' Recessed portion
83', 84' Release button
100' Organ fixing instrument
200' Fixing groove
300' Hollow portion
310' Through hole
320' Swaging portion
400' Hollow portion (String passage)
410' Slit
420' Flat portion
430' Fixed portion
500' Hollow portion
510' Slit
520' Fixed portion
600' Recessed portion
610' Convex portion
A' Body wall
B' Stomach wall

The invention claimed is:

1. A repeated type organ fixing instrument comprising:
a plurality of suturing tools, each comprising a rod-shaped engaging portion; and
a puncture needle for housing a plurality of the engaging portions, such that the plurality of the engaging portions can be extruded one by one from the puncture needle by operation of a operation unit main body,
wherein a suture fixed to at least one of the plurality of engaging portions is inserted within an inside of the puncture needle to entirely pass through the inside of the puncture needle toward the operation unit main body, and
wherein another suture fixed to one of the other engaging portions is derived from the inside of the puncture needle to be extended outside the puncture needle toward the operation unit main body.

2. The repeated type organ fixing instrument according to claim 1, wherein the puncture needle is provided with a penetrating portion which communicates between the inside and the outside of the puncture needle, through which said another suture passes is derived from the inside of the puncture needle to be extended outside the puncture need.

3. The repeated type organ fixing instrument according to claim 2, wherein the penetrating portion has a slit extending toward the operation unit main body from a needle tip which is the tip of the puncture needle.

4. The repeated type organ fixing instrument according to claim 3, wherein the plurality of suturing tools has three or more suturing tools, the slit extends from an arrangement region of the engaging portion located at a tip end side of the puncture needle to at least a middle of an arrangement region of the engaging portion located at a next stage of a base end side of the puncture needle, and wherein the suture of the engaging portion located at the next stage is inserted into the slit.

5. The repeated type organ fixing instrument according to claim 4, wherein the slit is formed in a spiral shape.

6. The repeated type organ fixing instrument according to claim 2, the instrument has a transverse hole penetrating inside and outside of the puncture needle as the penetrating portion.

7. The repeated type organ fixing instrument according to claim 6, wherein an end face of a tip end side of the traverse hole is inclined from a tip end direction to a base end direction as the end face goes from the inside of the puncture needle.

8. The repeated type organ fixing instrument according to claim 1, wherein the plurality of suturing tools has two suturing tools.

9. The repeated type organ fixing instrument according to claim 8, wherein an inner diameter of the puncture needle is a first total length or more, in which a minor axis of the engaging portion is added with a minor axis of the suture, and less than a second total length in which a major axis of the engaging portion is added with major axes of the two sutures.

10. The repeated type organ fixing instrument according to claim 1, wherein the plurality of suturing tools has three or more suturing tools, the sutures of the two suturing tools among three or more sutures, are derived from the inside to the outside of the puncture needle, and wherein the sutures are opposed with respect to the puncture needle.

11. A repeated type organ fixing instrument comprising a plurality of suturing tools, each of the suturing tools comprising a rod-shaped engaging portion, and a suture in which an end thereof is fixed to the engaging portion,
wherein the repeated type organ fixing instrument further comprising a puncture needle for housing a plurality of the engaging portions side by side in a tip base direction such that said plurality of the engaging portions can be extruded one by one from the puncture needle by operation of a operation unit main body, and
wherein a string passage for inserting the suture of the suturing tool housed at a tip end side into an inside of the puncture needle is formed at the engaging portion of the other suturing tool housed at a base end side,
wherein the engaging portion of the other suturing tool is formed into a hollow shape having a through hole to communicate with an inside and an outside of the hollow shape, the through hole being formed at a middle in a longitudinal direction of the engaging portion, wherein the suture of the suturing tool housed at the tip end side is fixed to the inside of the hollow shape by swaging around the engaging portion to pass through the through hole to the outside of the engaging portion.

12. The repeated type organ fixing instrument according to claim 11, wherein the inside of the hollow shape of the engaging portion is the string passage.

13. The repeated type organ fixing instrument according to claim 11, wherein a plurality of other string passages are formed on the engaging portion of the other suturing tool and the plurality of other string passages are formed and dispersed so as to be separated with each other.

14. The repeated type organ fixing instrument according to claim 13, the plurality of other string passages include three or more string passages and the plurality of other string passages are evenly formed and dispersed in a circumferential direction on a surface of the engaging portion.

* * * * *